United States Patent [19]
Chou et al.

[11] Patent Number: 5,504,053
[45] Date of Patent: Apr. 2, 1996

[54] ALKYLENE OXIDE CATALYSTS HAVING ENHANCED ACTIVITY AND/OR STABILITY

[75] Inventors: Pen-Yuan Chou; Madan M. Bhasin; Hwaili Soo; Erlind M. Thorsteinson, all of Charleston, W. Va.

[73] Assignee: Union Carbide Chemicals & Plastics Technology Corporation, Danbury, Conn.

[21] Appl. No.: 502,187

[22] Filed: Apr. 3, 1990

Related U.S. Application Data

[63] Continuation-in-part of Ser. No. 340,242, Apr. 18, 1989, and a continuation-in-part of Ser. No. 340,390, Apr. 18, 1989.

[51] Int. Cl.$^6$ .................................................. B01J 23/50
[52] U.S. Cl. ..................... 502/348; 502/208; 502/217; 502/218; 502/322; 502/324; 502/341; 502/344; 502/300; 549/536
[58] Field of Search ..................................... 502/208, 218, 502/314, 324, 347, 348, 217, 322, 341, 344; 549/536

[56] References Cited

U.S. PATENT DOCUMENTS

| | | | |
|---|---|---|---|
| 2,040,782 | 5/1936 | van Peski | 260/54 |
| 2,605,239 | 7/1952 | Sears | 252/475 |
| 2,615,900 | 10/1952 | Sears, Jr. | 260/348.5 |
| 2,769,016 | 10/1956 | Lichtenwalter et al. | 260/348.5 |
| 3,844,981 | 10/1974 | Cusumano | 252/471 |
| 3,962,285 | 6/1976 | Cusumano | 260/348.5 |
| 4,007,135 | 2/1977 | Hayden et al. | 252/467 |
| 4,761,394 | 8/1988 | Lauritzen | 502/348 |
| 4,766,105 | 8/1988 | Lauritzen | 502/216 |
| 4,800,070 | 1/1989 | Carlin et al. | 423/210.5 |

FOREIGN PATENT DOCUMENTS

| | | |
|---|---|---|
| 0247414 | 2/1984 | European Pat. Off. . |
| 57-136941 | 8/1982 | Japan . |
| 2095242 | 9/1982 | United Kingdom . |

OTHER PUBLICATIONS

"Influence of Feed Water Vapor on the Selective Oxidation of Ethylene over Silver Catalyst," *Applied Catalysis*, 61: 265–74 (1990).

Imamura, et al., "Effect of Samarium on the Thermal Stability and Activity of the Mn/Ag Catalyst in the Oxidation of CO", *J. of Catalysis*, vol. 115, pp. 258–264 (1989).

Lewis, "Decomposition of Silver Oxide by Autocatalysis", *Z. Physik Chem.*, 52:310–326 (1905).

Kendall, et al., "The Catalytic Influence of Foreign Oxides on the Decomposition of Silver Oxide, Mercuric Oxide and Barium Peroxide", *J. Amer. Chem. Soc.*, vol. 43, p. 2017 (1921).

Kripylo, et al., "Why Do Metal Oxide Dopings Stabilize the Dispersity of Silver Support Catalyst for the Selective Oxidation of Ethene", *Chem. Techn.*, 38(5) (1985).

Berger, et al., "Dependence of the Sintering of Polycrystalline Silver on the Gas Atmosphere", *Chem. Techn.*, 38(6):245–8 (1986).

*Primary Examiner*—Anthony McFarlane
*Attorney, Agent, or Firm*—J. B. Mauro

[57] ABSTRACT

Catalysts for the production of alkylene oxide by the epoxidation of alkene with oxygen comprise a silver impregnated support containing a sufficient amount of manganese component to enhance at least one of activity and/or efficiency and/or stability as compared to a similar catalyst which does not contain manganese component.

39 Claims, No Drawings

ALKYLENE OXIDE CATALYSTS HAVING ENHANCED ACTIVITY AND/OR STABILITY

This patent application is a continuation-in-part of U.S. patent application Ser. Nos. 340,242 and 340,390, both filed Apr. 18, 1989, and both herein incorporated by reference.

FIELD OF THE INVENTION

This invention relates to silver-containing, supported catalysts for the epoxidation of alkene, especially ethylene, to the corresponding alkylene oxide, e.g., ethylene oxide, which contain a stability and/or efficiency and/or activity enhancing amount of a manganese-containing component.

BACKGROUND OF THE INVENTION

Ethylene oxide is commercially produced by the epoxidation of ethylene over silver-containing catalyst at elevated temperature. Considerable research efforts have been devoted to providing catalysts that increase the efficiency, or selectivity, of the process to ethylene oxide.

The manufacture of ethylene oxide by the reaction of oxygen or oxygen-containing gases with ethylene in the presence of a silver catalyst is an old and developed art. For example, U.S. Pat. No. 2,040,782, patented May 12, 1936, describes the manufacture of ethylene oxide by the reaction of oxygen with ethylene in the presence of silver catalysts which contain a class of metal promoters. In U.S. Pat. No. Re. 20,370, dated May 18, 1937, Leforte discloses that the formation of olefin oxides may be effected by causing olefins to combine directly with molecular oxygen in the presence of a silver catalyst. From that point on, the prior art has focused its efforts on improving the catalyst's efficiency in producing ethylene oxide.

In characterizing this invention, the terms "conversion", "selectivity", and "yield" are employed as defined in U.S. Pat. No. 3,420,784, patented Jan. 7, 1969, at column 3, lines 24–35 inclusive. This definition of "selectivity" is consistent with that disclosed in U.S. Pat. No. 2,766,261 at column 6, lines 5–22, and U.S. Pat. No. 3,144,916, lines 58–61. The definitions of "yield" and "conversion" have more varied meaning in the art and are not to be employed as defined, for example, in the aforementioned U.S. Pat. No. 2,766,261. The terms "efficiency" and "selectivity", as used throughout the specification and claims are intended to be synonymous.

Silver catalysts employed in the manufacture of ethylene oxide have undergone significant changes since their initial period of development. As reported by the art, silver particles were first deposited upon support materials with little attention being paid to support properties, such as surface area, pore volume and chemical inertness. As the art evolved, there developed special technologies related to carriers or supports containing silver that were more effective for the reaction of ethylene with oxygen to produce ethylene oxide. Today, most supports for the silver catalyst, are shaped particulate materials which can be loaded in the interior of a reactor wherein the reacting gases and the gaseous products of the reaction are capable of flowing in and about these particulate materials to pass through the reactor and be recovered. The size and shape of the support are variable factors and the particular size and shape selected are peculiar to the reactor employed, the gas flow required, and the pressure drop across the reactor, with other factors also being considered.

The carriers that have been employed are typically made of inorganic materials, generally of a mineral nature. In most cases, the preferred carrier is made of alpha-alumina, such as has been described in the patent literature: see for example, U.S. Pat. Nos. 2,294,383; 3,172,893; 3,332,887; 3,423,328; and 3,563,914.

The carriers which are employed for the manufacture of most, if not all, commercially employed ethylene oxide catalysts are produced by companies who do not produce such catalysts. As a rule, the methods of making such carriers are trade secrets of significant value to the carrier manufacturers. Consequently, the catalyst manufacturer cannot know how the carrier is made. Critical to making a carrier which proves uniquely desirable for the manufacture of a successful catalyst can be a number of factors, such as the purity and other physical/chemical properties of raw materials used to make the carrier and the method by which the carrier is made.

The silver that is deposited on these carriers is thought to be in the form of small particles because that is all that can be seen by current microscopic techniques. The patent literature indicates that the size of the silver is a factor in the effectiveness of the catalyst and in most cases fine particle silver is obtained utilizing the standard processes in the art; see, for example, U.S. Pat. Nos. 2,554,459; 2,831,870; 3,423,328 (specifies that silver particles of 150–400 Angstroms are employed); 3,702,259 (disclosed a preparation procedure for forming silver particles less than 1 micron in diameter) and 3,758,418 (discloses silver particles having a diameter less than 1000 Angstroms). Improvements in microscopic examinations of silver catalysts enable the observation that the particle size ranges to even smaller values.

The deposition of silver onto the carrier can be achieved by a number of techniques but the two techniques which are most frequently employed involve, in one case, the impregnation of the support with a silver solution followed by heat treatment of the impregnated support to effect deposition of the silver on the support and, in the other case, the coating of the silver on the support by the precipitation of silver or the preformation of silver into a slurry such that the silver particles are deposited on the support and adhere to the support surface when the carrier or support is heated to remove the liquids present. These various procedures are exemplified in various U.S. Pat. Nos. such as 2,773,844; 3,207,700; 3,501,407; 3,664,970 (see British Patent 754, 593) and 3,172,893.

The surface area provided by the support has been the subject of considerable interest in the development of silver catalysts. Disclosures concerning the surface area of the catalyst carrier can be found in U.S. Pat. No. 2,766,261 (which discloses that a surface area of 0.002–10 $m^2$/gm is suitable); U.S. Pat. No. 3,172,893 which depicts a porosity of 35–65% and a pore diameter of 80–200 microns); U.S. Pat. No. 3,725,307 which depicts a surface area of less than 1 sq.m/gm and an average pore diameter of 10–15 microns): U.S. Pat. No. 3,664,970 (which utilizes a support having a minimum porosity of about 30%, at least 90% of the pores having diameters in the range of 1–30 microns, and the average of such diameters being in the range of 4–10 microns); and U.S. Pat. No. 3,563,914 which utilizes a catalyst support having a surface area of less than 1 sq.m/ gm, a volume of 0.23 ml/gm and a particle size between 0.074 and 0.30 mm). Low surface area, inert alpha-alumina is favored by the prior art.

It has been known for a long time that impurities present in the catalyst and/or the gas phase can materially impact upon the reaction. In the early development of the art, there were no techniques available for identifying or measuring such impurities. Consequently, one could not isolate the role that such impurities played. However, even in the earliest periods of the development of the art, the use of alkali metals as promoters for the silver catalyzed production of ethylene oxide was extremely well known in the art. U.S. Pat. No. 2,177,361, issued October 1939, has a teaching of the use of alkali metals in silver catalysts. U.S. Pat. No. 2,238,471 discloses that lithium is very desirable as a promoter but that potassium and cesium are detrimental when used in amounts of essentially 10% by weight of potassium hydroxide or cesium hydroxide to the silver oxide employed in making the catalyst. Later, U.S. Pat. No. 2,404,438 states that sodium and lithium are effective promoters for this reaction. Essentially the same teaching can be found in U.S. Pat. No. 2,424,084. U.S. Pat. No. 2,424,086 generalizes about alkali metals as promoters and specifies sodium in particular. In U.S. Pat. No. 2,671,764 (the Sacken sulfate patent), the patentees believe that alkali metals in the form of their sulfates are effective as promoters for such silver catalysts. In particular, the patentees state that sodium, potassium, lithium, rubidium or cesium sulfates may be used as promoters.

U.S. Pat. No. 2,765,283 describes the pretreatment of a support with a dilute solution of a chlorine-containing compound and indicates that such chlorine compounds should be inorganic. Particular illustrations cited of suitable inorganic chlorine compounds included sodium chloride, lithium chloride and potassium chlorate. This patent specifies that the amount of the inorganic chlorine-containing compound which is deposited on the catalyst support is from 0.0001% to 0.2% by weight based on the weight of the support, U.S. Pat. No. 2,615,900 to Sears describes the use of metal halide in the treatment of the supported catalyst and specifies that such halides can be of alkali metals such as lithium, sodium, potassium and cesium. The metal halide is present in the range of 0.01% to 50% based upon the weight of metallic silver. The patent also specifies that mixtures of the individual metal halides generally classified in the patent may be used to advantage to enhance the break-in period of a new catalyst composition while at the same time maintaining a moderate but steady activity of the catalyst over an extended period of time during normal operation. Thus, one particular metal halide treated catalyst would provide a short-term high initial activity whereas another of the metal halides would provide a longer term moderate activity for the catalyst. This patent takes the position that the metal halides which are provided in the catalyst serve to inhibit the combustion of ethylene to carbon dioxide and thus classifies these materials as catalyst depressants or anticatalytic materials.

U.S. Pat. No. 2,709,173 describes the use of a silver catalyst for making ethylene oxide in which there are provided simultaneously with the introduction of silver to the solid support, any of the alkali metal halides such as lithium, sodium, potassium, and rubidium compounds of chlorine, bromine and iodine, to enhance the overall production of ethylene oxide. The patent specifies small amounts "of less than about 0.5% are desirable." In particular, the patent emphasizes "proportions of alkali metal halide within the range of about 0.0001 to about 0.1" are most preferred. The patent states that "although the preferred catalyst composition contains a separate promoter it is not always necessary since during preparation of the catalyst the alkali metal halide may be converted to some extent to the corresponding alkali metal oxide which acts as a promoter."

U.S. Pat. No. 2,766,261 appears to draw from the teachings of U.S. Pat. No. 2,238,474 in that cesium and potassium are said to be detrimental in silver catalysts; sodium and lithium are suggested as useful promoters. However, U.S. Pat. No. 2,769,016 finds that sodium, potassium and lithium are promoters when used in the silver catalysts. This latter patent also recommends the pretreatment of the support with dilute solutions of sodium chloride, lithium chloride or potassium chlorate.

U.S. Pat. No. 2,799,687 to Gould, et al., states that the addition of metal halides within the range described by Sears in U.S. Pat. No. 2,615,900 is not productive of optimum results. This is said to be especially true in the case of alkali metal halides, particularly the chloride and fluoride of sodium and potassium. The patentees recommend that the inorganic halide component of the catalyst be maintained within the range of 0.01–5 weight percent, preferably 0.01 to 0.1 weight percent, based on the weight of the "silver oxidative catalytic component," i.e., the silver salt transformed into elemental silver. U.S. Pat. No. 3,144,416 mentions a variety of metals as promoters and one of them is cesium. U.S. Pat. No. 3,258,433 indicates that sodium is an effective promoter. U.S. Pat. No. 3,563,913 recommends the use of alkali metals such as lithium compounds as promoters. The preferred amount of promoting material is said to be about 0.03 to 0.5%, by weight of metal oxide based on the weight of the support. U.S. Pat. No. 3,585,217 states that alkali metal chlorides "are known to counteract the formation of carbon dioxide" and "may be incorporated into the catalyst." U.S. Pat. No. 3,125,538 discloses a supported silver catalyst containing a coincidentally-deposited alkali metal selected from among potassium, rubidium and cesium in a specified gram atom ratio relative to silver. The weight of silver is preferably 2–5% by weight of the catalyst. The patentees characterize this catalyst as being especially suitable for the reaction of nitric oxide with propylene. This same catalyst is produced inherently by the processes of the examples of U.S. Pat. No. 3,702,259, as discussed previously, which patent promotes their use for making ethylene oxide. U.S. Pat. Nos. 3,962,136 and 4,012,425 also disclose that same catalyst as being useful for ethylene oxide production. U.S. Pat. No. 3,962,136 describes the coincidental deposition of alkali metal with the silver on the support, the alkali metals being present in their final form on the support in the form of an oxide in which the oxide consists of cesium, rubidium or mixtures of both, optionally combined with a minor amount of an oxide of potassium. The amount of such oxide is from about $4.0 \times 10^{-5}$ gew/kg to about $8.0 \times 10^{-3}$ gew/kg of total catalyst. U.S. Pat. No. 4,356,312 describes the use of the same catalyst. U.S. patent application Ser. No. 317,349, filed Dec. 21, 1972, which is a parent to U.S. Pat. Nos. 3,962,136 and 4,010,115 and others, contains some interesting data deserving of comment. According to example 2 which contains some comparative experiments, there is described the manufacture of a catalyst which contains 310 parts per million by weight of coincidentally-added potassium and that catalyst when employed as an ethylene oxidation catalyst was found to be inactive for the production of ethylene oxide.

U.S. Pat. No. 4,207,210 (cortes. Belgium Patent 821,439, based upon British Patent Specification 1,489,335) discloses that a catalyst can be made that is equivalent to that produced in the so-called parent applications cited in U.S. Pat. Nos. 3,962,136, 4,012,425, and 4,010,115 by using a sequential procedure by which the alkali metal is supplied to the support. Thus, the criticality in the method of deposition of alkali metal in the catalyst appears doubtful in the face of that type of disclosure and the disclosure of U.S. Pat. Nos. 4,033,903 and 4,125,480 which describe subjecting used silver-containing catalysts to a post-addition of one or more of potassium, rubidium or cesium. Apparently, such treatment regenerates the catalyst's ability to enhance selectivity to ethylene oxide. Another patent which tends to indicate that a post-addition of alkali metal such as cesium gives results equivalent to either pre-addition or simultaneous addition is U.S. Pat. No. 4,066,575.

German Offenlegungsschrift 2,640,540 discloses in its examples a silver catalyst for ethylene oxide production containing sodium and either potassium, rubidium or cesium.

Japanese Application Publication Disclosure No. 95213/75 is directed to a process for producing ethylene oxide using a catalyst composition comprising silver, barium, potassium and cesium in specified atomic ratios. Table I of this disclosure summarizes the efficiencies achieved with the various catalyst compositions of the examples.

U.S. Pat. No. 4,039,561 discloses a catalyst for preparing ethylene oxide containing silver, tin, antimony, thallium, potassium, cesium and oxygen in specified atomic ratios.

Belgium Patent 854,904 discloses silver catalysts containing various mixtures of sodium and cesium. U.K. Patent Application 2,002,252 discloses, in Table 2, supported silver catalysts containing various mixtures of cesium and thallium, some of which additionally contain potassium or antimony. U.S. Pat. No. 4,007,135 broadly discloses (in column 2, lines 25–30) silver catalysts for alkylene oxide production containing silver "together with a promoting amount of at least one promoter selected from lithium, potassium, sodium, rubidium, cesium, copper, gold, magnesium, zinc cadmium, strontium, calcium, niobium, tantalum, molybdenum, tungsten, chromium, vanadium and barium . . . ". U.S. Pat. Nos. 3,844,981 and 3,962,285 disclose catalysts and processes for epoxidizing olefins in the presence of a multimetallic component. The catalyst in the U.S. Pat. No. 3,962,285 is said to comprise a minor amount of one or more of palladium, ruthenium, rhenium, iron and platinum with a major amount of silver. The U.S. Pat. No. 3,844,981 discloses the preparation of the catalyst from a decomposible salt of group 7b, 1b or the iron group of group 8 of the Periodic Table of the Elements. Preferably, the salt is selected from the group of gold, copper, rhenium, manganese and iron salts. While the patentee contemplates that these metals are in the metallic state, oxidation during epoxidation conditions may occur with one or more of these metals, e.g., rhenium, to form oxyanions containing the metal.

U.S. Pat. No. 2,605,239 discloses the use of beryllium oxide as a promoter. Other promoter metals such as copper, aluminum, manganese, cobalt, iron, magnesium, gold, thorium, nickel, cesium and zinc are suggested. These promoter metals are to be incorporated into the catalyst by mechanical mixture or coprecipitation.

European Patent Publication No. 0003642 discloses, in Table 3, silver-containing catalysts which include mixtures of potassium and cesium, and a catalyst containing sodium and cesium.

Belgium Patent 867,045 discloses supported silver catalysts containing what is referred to as an effective proportion of lithium and a substantially lesser amount of alkali metal selected from among cesium, rubidium and/or potassium.

Belgium Patent 867,185 discloses supported silver catalysts for ethylene oxide production containing a specified amount of potassium and at least one other alkali metal selected from rubidium and cesium.

United Kingdom Patent No. 2,043,481, commonly assigned, describes the use of a synergistic combination of cesium and at least one other alkali metal in combination with silver on an inert support to provide catalysts which were superior to those known to the art at that time. Such catalysts have been widely employed commercially. The alkali metal components are provided to the support by a variety of ways. The alkali metal can be supplied to the support as a salt and many salts of the alkali metals are described. Specific illustration is made of the use of alkali metal sulfates as one of many usable alkali metal compounds.

European Patent Application 85,237 describes an ethylene oxide catalyst wherein the applicants believe they "chemically absorbed" by alcohol wash, cesium and/or rubidium onto the catalyst support.

Japanese patent application Kokai 56/105,750 discloses, among other things, ethylene oxide catalysts containing cesium molybdate or cesium tungstate or cesium borate. The catalyst is stated to have an alumina carrier having a sodium content of less than 0.07 weight % and mainly consisting of alpha-alumina having a specific surface area of 1 to 5 sq. m./gm. The carrier is impregnated with decomposible silver salt solution containing alkali metal boron complex, alkali metal molybdenum complex and/or alkali metal tungsten complex. No examples of mixtures of anions are disclosed. Japanese patent application Kokai 57/21937 discloses thallium-containing catalysts in which the thallium may be borate or titanate salt.

European patent application 247,414, published Dec. 12, 1987, discloses catalysts containing alkali metal and/or barium which may be provided as salts. The salts include nitrates, sulfates, and halides. U.S. Pat. Nos. 4,761,394 and 4,766,105 disclose catalysts containing a rhenium component, e.g., rhenium oxide, rhenium cation or rhenate or perrhenate anion. An example of a catalyst made from silver oxalate with cesium hydroxide, ammonium perrhenate, and ammonium sulfate is disclosed in the '394 patent. Numerous examples of silver catalysts containing cesium, rhenate and co-promoter salts are presented in the '105 patent. Experiments 7-1, 7-2, 7-3, 7-4, 7-12 and 7-27 as reported in the '105 patent are summarized below.

| Experiment | Ag, % | Cs, ppm | Re, ppm | Other Component, ppm | Initial $S_{40}$, % | Initial $T_{40}$, °C. |
|---|---|---|---|---|---|---|
| 7-1 | 14.3 | 236 | 0 | None | 80.0 | 242 |
| 7-2 | 13.9 | 360 | 186 | None | 80.6 | 241 |
| 7-3 | 14.2 | 438 | 372 | None | 81.9 | 248 |
| 7-4 | 13.3 | 405 | 186 | $(NH_4)_2SO_4$, 32(S) | 83.1 | 259 |
| 7-12 | 13.5 | 328 | 186 | $KMnO_4$, 55(Mn) | 80.8 | 242 |
| 7-27 | 14.3 | 293 + 7Li | 186 | $(NH_4)_2SO_4$, 32(S) | 82.4 | 245 |

$S_{40}$ and $T_{40}$ are defined in the patent and are the efficiency and temperature at 40 percent oxygen conversion as determined at about 16±4 hours.

Several phenomena appear to be discernible from these data. Rhenate appears to enhance efficiency, especially in the presence of certain "co-promoters" such as sulfate anion. Furthermore, when the amount of rhenate is increased or a copromoter is used which increases efficiency, the temperature required for 40 percent oxygen conversion ("$T_{40}$, °C.") also appears to increase in most instances. The presence of 55 ppm Mn as $KMnO_4$ in Experiment 7–12 appears to have little, if any, effect on $S_{40}$ (selectivity at 40 mol % oxygen conversion) or $T_{40}$.

While improved efficiencies of conversion to ethylene oxide are desirable, the concomitant increase in temperature (i.e., loss of activity) can be troublesome for a commercially-viable catalyst. Commercial ethylene oxide plants are typically operated to provide a desired balance of productivity and efficiency. Less active catalysts are thus operated at higher temperatures to achieve desired productivity. However, the upper temperature range of the catalyst is limited. Consequently, catalysts that have high initial temperatures for a given conversion rate may have shorter useful lives. Not only is catalyst a major expense to the ethylene oxide plant owner, but also, the plant must be shut down for substantial periods of time to discharge the old catalyst and charge new catalyst to the typical tubular, fixed bed ethylene oxide reactors. Hence, without a useful lifetime, e.g., two years or more, the benefit of any enhanced efficiency is quickly lost in catalyst replacement costs and plant shut-down time.

U.S. patent applications Ser. Nos. 18,808, filed Feb. 20, 1987, now abandoned; 640,269, filed Aug. 13, 1984, now abandoned; and 251,573 and 251,814, both filed Oct. 3, 1988, M. M. Bhasin, disclose silver-containing, supported catalysts for ethylene oxide production containing cesium salts of oxyanions having an atomic number of at least 15 to 83 and being from groups 3b through 7b and/or groups 3a through 7a of the Periodic Table of the Elements (as published by The Chemical Rubber Company, Cleveland, Ohio, in *CRC Handbook of Chemistry and Physics*, 46th Edition, inside back cover). The oxyanions include, by way of illustration, sulfate, phosphates, manganates, titanates, tantalates, molybdates, vanadates, chromates, zirconares, polyphosphates, tungstates, cerates, and the like. The following table summarizes several examples contained in the '573 patent application

| Example No. | Ag, % | Cs Salt, Amount | Other Salt, Amount | Efficiency, % | Temperature, °C. |
|---|---|---|---|---|---|
| 15 | 13.09 | 0 | 0 | 73.5 | 238 |
| 23 | 13.55 | CsMnO$_4$, 0.0101% | 0 | 79.7 | 240 |
| 29 | 13.25 | CsMnO$_4$, 92 ppm Cs | KMnO$_4$, 27 ppm K | 79.6 | 249 |
| 30 | 13.25 | CsMnO$_4$, 95 ppm Cs | KMnO$_4$, 28 ppm K H$_2$SO$_4$, 48 ppm | 76.0 | 254 |
| 34 | 14.1 | CsMnO$_4$, 51 ppm Cs | KMnO$_4$, 152 ppm K | 59.6 | 281 |

Examples 15, 23, 29, and 30 were conducted under oxygen process conditions and Example 34 was conducted under air process conditions. Oxygen and air process conditions are generally described herein.

Manganese has been proposed for use in catalysts for other applications. For instance, United Kingdom patent application 2,095,242A, published Sep. 29, 1982, discloses the oxychlorination of alkanes in the presence of a solid particulate catalyst composition comprising (1) metallic silver and/or a compound thereof and (2) one or more compounds of manganese, cobalt or nickel. Japanese patent application Kokai 57/136941, published Aug. 24, 1982, discloses catalysts for the decomposition of ozone. The catalyst appears to be made by adding 0.1 to 20 weight percent of silver and 1 to 20 weight percent of cobalt oxide (calculated as atomic percent of cobalt) to manganese dioxide. Imamura, et al., in "Oxidation of Carbon Monoxide Catalyzed by Manganese-Silver Composite Oxides", *J. of Catalysis*, vol. 109, pp 198–205 (1988) and "Effect of Samarium on the Thermal Stability and Activity of the Mn/Ag Catalyst in the Oxidation of CO", *J. of Catalysis*, vol. 115, pp 258–264 (1989) disclose manganese-silver catalysts for the catalytic oxidation of carbon monoxide. U.S. Pat. No. 4,800,070 is directed to the catalysis of a nitrate-nitrite system for the separation of oxygen from oxygen-containing gases such as air. The catalyst comprises transition metal oxide selected from the group consisting of oxides of manganese, ruthenium, rhenium, osmium, rhodium, iridium and mixtures thereof.

Methods are sought to enhance the activity and/or stability of silver-containing, supported ethylene oxide catalysts which have been promoted to enhance efficiency, which while providing desirable efficiencies, are typically less active and must be operated at higher temperatures to be useful in commercial production facilities. These high temperatures can unduly-shorten the catalyst life such that the catalysts are unattractive for commercial facilities.

SUMMARY OF THE INVENTION

By this invention silver-containing, supported alkylene oxide catalysts suitable for the epoxidation of alkene to alkylene oxide are provided that have enhanced activity and/or efficiency and/or stability. The catalysts contain deposited thereon a sufficient amount of at least one manganese component to increase at least one of the activity and/or efficiency and/or stability of the catalyst as compared to a similar catalyst but not containing the manganese component under otherwise identical conditions. Often, the manganese component is present in an amount of at least about 20 or 60, e.g., about 70 to 1000, preferably 80 to 500, ppm (weight) calculated as the weight of manganese based on the total weight of the catalyst. The amount of manganese which provides the enhanced activity and/or efficiency and/or stability generally varies depending on the nature and amounts of other components in the catalyst composition.

The catalysts of this invention preferably contain an amount of activity-enhancing manganese component at least sufficient to increase activity of the catalyst, as determined under Standard Ethylene Oxide Process Conditions (herein defined), by at least about 5° C., preferably at least about 10° C.

When the activity of a catalyst is enhanced, the temperature required to produce, under given conditions, a given level of alkylene oxide (usually expressed in terms of increase in alkylene oxide concentration across the catalyst bed) is reduced. The stability of a catalyst can be with respect to at least one of efficiency aging rate and activity aging rate. In a more stable catalyst, the efficiency aging rate and/or activity aging rate is less than that in a less stable catalyst.

As used herein, the term "compound" refers to the combination of a particular element with one or more different elements by surface and/or chemical bonding, such as ionic and/or covalent and/or coordinate bonding. The term "ionic" or "ion" refers to an electrically chemical charged moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions.

The catalyst preferably contains at least one other promoter in an amount sufficient to enhance the efficiency of the catalyst as compared to a similar catalyst but not containing the promoter. Often, the promoter comprises a compound of an element other than manganese which is selected from Groups 1a and/or 2a and/or from Groups 3b to 7b or 3a to 7a of the Periodic Table. (References to the Periodic Table herein shall be to that as published by the Chemical Rubber Company, Cleveland, Ohio, in *CRC Handbook of Chemistry and Physics,* 46th Edition, inside back cover.) The preferred promoters include the oxyanions of the elements other than oxygen having a molecular weight of 5 to 83 of Groups 3b to 7b and 3a to 7a of the Periodic Table. Most preferably, the promoters are one or more of the oxyanions of nitrogen, sulfur, tantalum, molybdenum, tungsten and rhenium. Many of these promoters are characterized as both increasing efficiency and reducing activity of the catalysts. Catalysts containing combinations of promoters such as sulfate with one or more of oxyanions of Group 3b to 7b elements such as molybdenum and rhenium often have their activities significantly increased by the presence of the manganese component.

In another preferred aspect of this invention, the catalysts contain a rhenium component which may be in the form of a cation or an anion, e.g., rhenate.

In one preferred aspect of this invention, the epoxidation of alkene in the presence of an oxygen-containing gas comprises contacting the alkene and the catalyst under epoxidation conditions in the presence of at least one efficiency-enhancing gaseous member of a redox-half reaction pair. The catalyst comprises as a promoter, an efficiency-enhancing amount of at least one efficiency-enhancing salt of a member of a redox-half reaction pair.

In yet another preferred aspect of the invention, the catalyst comprises alkali metal nitrate, especially potassium and/or rubidium nitrate, especially in amounts greater than about 400 or 500 parts per million (ppm) by weight based on the weight of potassium. In this aspect of the invention, a nitrogen and oxygen-containing compound, e.g., nitrogen oxide, nitrogen dioxide, nitrous oxide, etc., may be introduced into the reaction zone containing the catalyst as a copromoter to enhance at least one of activity, efficiency and stability of the catalyst performance.

In a further preferred aspect of the invention, the catalyst contains less than about 50 ppmw, and most preferably less than 25 ppmw, leachable potassium. At these low potassium levels, the enhancing effect of the manganese component may, in some instances, be more pronounced.

An aspect of this invention relates to the use of the aforementioned catalysts in epoxidizing alkene to alkylene oxide, especially ethylene to ethylene oxide.

DETAILED DISCUSSION

Alkylene oxides made using the catalysts of this invention are characterized by the structural formula

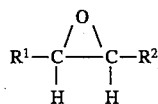

wherein $R^1$ and $R^2$ are lower alkyl, e.g., methyl or ethyl or, preferably, hydrogen. Most preferably the alkylene oxide is ethylene oxide. The alkylene oxides are made from the corresponding alkene, i.e., $R^1HC=CHR^2$. For purposes of ease of understanding, the following discussion will be made with reference to ethylene oxide and ethylene.

The catalysts of this invention are characterized by combining a sufficient amount of at least one manganese component to enhance the activity and/or efficiency and/or stability of the catalyst as compared to a similar catalyst which does not contain the manganese component. Although the catalysts can be used under widely varying process conditions, for purposes of determining whether sufficient manganese component has been incorporated into the catalyst, a standard set of process conditions can be used.

The STANDARD ETHYLENE OXIDE PROCESS CONDITIONS (ABBR. "CONDITIONS") for characterizing the catalysts of this invention involve the use of a standard backmixed autoclave with full gas recycle including carbon dioxide. The CONDITIONS may be operated with some variation in ethylene, oxygen and gas phase inhibitor feed. Two cases are illustrated: air process conditions, which simulates in the backmixed reactor the typical conditions employed in commercial air-type ethylene oxide processes where air is used to supply the molecular oxygen and the oxygen process conditions, which simulates in the backmixed reactor the typical conditions in commercial oxygen-type ethylene oxide processes where molecular oxygen, as such, is employed. Each case provides a different efficiency but it is the rule for practically all cases that air as the oxygen feed, using lower amounts of oxygen and ethylene will yield an efficiency to ethylene oxide which is about 2 to 4 percentage points lower than that when molecular oxygen is employed as oxygen feed. When the catalyst contains a redox-half reaction pair salt and is intended to be used in conjunction with the corresponding efficiency-enhancing gaseous member of a redox-half reaction pair, the CONDITIONS provide for the presence of such gaseous member. The CONDITIONS employ 1.0 mole % ethylene oxide in the outlet gas of the reactor under the following standard inlet conditions:

| Component | Air process Conditions, Mole % | Oxygen process Conditions, Mole % |
|---|---|---|
| Oxygen | 6.0 | 8.0 |
| Ethylene | 8.0 | 30 |
| Ethane | 0.5 | 0.5 |
| Carbon Dioxide | 6.5 | 6.5 |
| Nitrogen | Balance of Gas | Balance of Gas |
| Parts per million ethyl chloride (or one-half such amount when ethylene dichloride is used) | Optimum for Efficiency | Optimum for Efficiency |
| Parts per million gaseous member of reaction-half pair (when required for catalyst) | Optimum for Efficiency | Optimum for Efficiency |

The CONDITIONS employ the well known backmixed bottom-agitated "Magnedrive" autoclaves described in FIG. 2 of the paper by J. M. Betty entitled "Reactor for Vapor Phase-Catalytic Studies", in *Chemical Engineering Progress, Vol.* 70, No. 5, pages 78–84. 1974.

The pressure is maintained constant at 275 psig and the total outlet flow is maintained at 22.6 SCFH. SCFH refers to cubic feet per hour at standard temperature and pressure, namely, 0° C. and one atmosphere. The outlet ethylene oxide concentration is maintained at 1.0% by adjusting the reaction temperature. Thus temperature (°C.) and catalyst efficiency are obtained as the responses describing the catalyst performance.

The catalyst test procedure used in the CONDITIONS involves the following steps:

1. 80 cc of catalyst is charged to the backmixed autoclave. The volume of catalyst is measured in a 1 inch I.D. graduated cylinder after tapping the cylinder several times to thoroughly pack the catalyst. The volume of catalyst is alternatively calculated from the packing density of the carrier and the amount of silver and additives. The weight of the catalyst is noted.

2. The backmixed autoclave is heated to about reaction temperature in a nitrogen flow of 20 SCFH with the fan operating at 1500 rpm. The nitrogen flow is then discontinued and the above-described feed stream is introduced into the reactor. The total gas outlet flow is adjusted to 22.6 SCFH. The temperature is adjusted over the next few hours so that the ethylene oxide concentration in the outlet gas is approximately 1.0%.

3. The outlet oxide concentration is monitored over the next 4–6 days to make certain that the catalyst has reached its peak steady state performance. The temperature is periodically adjusted to achieve 1% outlet oxide. The selectivity of the catalyst to ethylene oxide and the temperature are thus obtained.

The standard deviation of a single test result reporting catalyst efficiency in accordance with the procedure described above is about 0.7% efficiency units. The standard deviation of a single test result reporting catalyst activity in accordance with the procedure described above is about 1.2° C. The standard deviation, of course, will depend upon the quality of the equipment and precision of the techniques used in conducting the tests, and thus will vary. The test results reported herein are believed to be within the standard deviation set forth above. The running of a multiplicity of tests will reduce the standard deviation by the square root of the number of tests.

The amount of manganese component is generally sufficient to provide an increase in activity under Standard Ethylene Oxide Process Conditions of at least 5° C., preferably at least 10° C. Most desirably, oxygen process conditions are used. In determining the increase in activity, the process and catalyst should be under steady state conditions, and can often be ascertained promptly upon steady state conditions being achieved. In some instances, the catalyst activates over a period of time, even as much as a week or more, before the catalyst reaches peak initial activity. The reason for this period of activation in some catalysts is not known and may be due to chemical and/or physical conditioning of the catalyst. Therefore, the activity is usually determined after the catalyst has been on-stream for at least 24, preferably, about 120 to 170, hours.

The optimal amount of the manganese component may vary with silver content, the amounts and types of other promoters present and the chemical and physical properties of the carrier. However, the manganese component is often present in an amount of at least 60 ppmw (parts per million by weight) calculated as the weight of manganese. If too much manganese component is used, the catalyst performance, e.g., efficiency and/or activity, may suffer. If too little manganese component is present, it is also possible that the performance of the catalyst will suffer. In determining desired amounts of manganese component, a traverse of manganese component concentrations in the catalyst composition can be effected with the catalysts being evaluated for performance. In some instances, it may be desirable to vary the amounts of other components, e.g., silver and other promoters, to achieve beneficial combinations of effects and optimal catalyst performances. Usually, the amount of manganese component falls within the range of about 70 to 1000, preferably, 80 to 500, ppmw calculated as the weight of manganese.

The manganese component can be provided in various forms, e.g., as a covalent compound such as manganese dioxide, as a cation or as an anion such as a manganate anion. The manganese species that provides enhanced activity and/or stability is not certain and may be the component added or that generated either during catalyst preparation or during use as a catalyst. Although the manganese species that provide the beneficial properties to the catalysts are not known with specificity, generally better results are obtained when the manganese component is added to catalyst in the form of permanganate ($MnO_2^-$). Higher oxidation states manganese such as manganate ($MnO_4^-$) as well as manganese as a cation (e.g., $Mn(NO_3)_2$) may be used, but with some activation time being required. Moreover, different added manganese components may also have different optimum concentrations to achieve the results. Often, the manganese in the manganese component has an oxidation state of +2, +3, +4 and/or +7, preferably +3, +4 and/or +7.

Manganese components include, but are not limited to, manganese acetate, manganous ammonium sulfate, manganese citrate, manganese dithionate, manganese oxalate, manganous nitrate, manganous sulfate, and manganate anion, e.g., permanganate anion, manganate anion, and the like. When in the form of an anion, the manganese component may be provided as an acid, or most frequently, a salt, e.g., of a group 1a, 2a, 1b or 2b salt or an ammonium salt, e.g., alkali or alkaline earth metal salts such as lithium, sodium, potassium, rubidium, cesium, beryllium, magnesium, calcium, strontium, barium, etc. Mixtures of manganate components may also be used.

As with any catalyst for making ethylene oxide which provides optimum performance, a correlation exists among many factors. Factors frequently considered include:

(i) the nature of the support;

(ii) the amount of silver on or in the support;

(iii) the components and amounts thereof in or on the support;

(iv) the impurities or contaminants provided with the silver or other components;

(v) the procedure to make the catalyst; and (vi) the conditions under which the catalyst is used to produce ethylene oxide.

However, in attempting to define any catalyst, there must be a base value from which other factors are determined especially when the factors are variables, each dependent upon the base value for meaning. In the case of this invention, the base value can be the amount of silver or a combination of the amount of silver and the nature of the support. In most cases the latter combination will be the base value. Because at least two values will comprise the base value for catalyst performance, it is apparent that correlations between such combinations and other factors can be quite complex. There is no common thread of logic which integrates all of these combinations and/or factors. To that extent, practice of the invention requires experimental efforts to achieve all or essentially all of the benefits of this invention. Without departing from this script, one skilled in the art can readily achieve the optimum performances of the catalysts of this invention. It should be recognized that such script is commonly followed by the artisan in making any commercially-employable ethylene oxide catalyst. The elements of the script are dependent upon the technology employed in making the catalyst.

The concentration of silver in the finished catalyst may vary from about 2 to 45 or more, often about 2 to 40 or more, weight percent, a commercially preferred range being from about 6% to about 35% by weight of silver. Lower silver concentrations are preferred from an economic standpoint. However, the optimum silver concentration for any particular catalyst will be dependent upon economic factors as well as performance characteristics, such as catalyst efficiency, rate of catalyst aging and reaction temperature.

In some catalysts of this invention, discrete silver particles on the finished catalyst and/or on used catalyst have an angular or irregular appearance, which sometimes may appear to be generally parallelepiped, and even generally cubic, as opposed to generally spherical or hemispherical as with catalysts such as disclosed in U.S. Pat. No. 3,702,259. The particles often have a major dimension of less than about 0.2, often less than about 0.1, micron.

The support or carrier employed in these catalysts in its broadest aspects is selected from the large number of porous refractory catalyst carriers or support materials which are considered relatively inert in the presence of the ethylene epoxidation feeds, products and reaction conditions. Many such materials are known to persons skilled in the art and may be of natural or synthetic origin and preferably are of a macroporous structure.

The chemical composition of the carrier is not narrowly critical. Carriers may be composed, for example, of alpha-alumina, silicon carbide, silicon dioxide, zirconia, magnesia and various clays. The preferred carriers are alpha-alumina particles often bonded together by a bonding agent and have a very high purity, i.e., at least 98 wt. % alpha-alumina, any remaining components being silica, alkali metal oxides (e.g., sodium oxide) and trace amounts of other metal-containing and/or non-metal-containing additives or impurities; or they may be of lower purity, i.e., about 80 wt. % alpha-alumina, the balance being a mixture of silicon dioxide, various alkali oxides, alkaline earth oxides, iron oxides, and other metal and non-metal oxides. The carriers are formulated so as to be inert under catalyst preparation and reaction conditions. A wide variety of such carriers are commercially available. Alumina carriers are manufactured by United Catalysts, Inc., Louisville, Ky., and the Norton Company, Akron, Ohio.

In the case of alpha alumina-containing supports, preference is given to those having a specific surface area as measured by the B.E.T. method of from about 0.03 $m^2/g$ to about 10 $m^2/g$, preferably from about 0.05 to about 5, more preferably from about 0.1 to about 3 $m^2/g$, and a water pore volume as measured by conventional water absorption techniques of from about 0.1 to about 0.85 cc/g by volume. The B.E.T. method for determining specific surface area is described in detail in Brunauer, S., Emmet, P. and Teller, E. *J. Am. Chem. Soc.*, 60, 309–16 (1938).

Certain types of alpha alumina-containing supports are particularly preferred. These alpha alumina supports have relatively uniform pore diameters and are more fully characterized by having (1) B.E.T. specific surface areas of from about 0.1 $m^2/g$ to about 3.0 $m^2/g$, preferably about 0.1 $m^2/g$ to about 2.0 $m^2/g$ and (2) water pore volumes of from about 0.10 cc/g to about 0.85 cc/g, preferably from about 0.25 cc/g to about 0.75 cc/g. Median pore diameters for the above-described carriers range from about 0.01 to 100 microns, a more preferred range being from about 0.5 to 50 microns. The carriers may have monomodal, bimodal or multimodal pore distributions. Typical properties of some supports found in the literature are shown in Table I.

TABLE I

| Carrier | A | B | C | D | E | F |
|---|---|---|---|---|---|---|
| B.E.T. Surface Area $m^2/g$[a] | 0.21 | 0.42 | 0.42 | 0.48 | 0.57 | 2.06 |
| Water Pore Volume, cc/g | 0.26 | 0.36 | 0.41 | 0.49 | 0.44 | 0.65 |
| Crush Strength, FPCS, lbs[b] | 100% 20 lbs | 97% 15 | Avg. 21 Range 15–30 | 90% 14 | 90% 15 | No Data |
| Total Pore Volume, Hg, cc/g[c] | 0.26 | 0.42 | 0.42 | 0.46 | 0.42 | 0.65 |
| Average Pore Diameter, Hg, Angstroms[c] | 620 | 560 | 640 | 550 | 770 | 1000 |
| Median Pore Diameter, Hg, microns[c,e] | 3.7 | 2.7 | 3.4 | 3.4 | 2.4 | 2.5 |
| Percent Pore Volume in Pores Greater than 350 Angstroms[c] | 90.0% | 88.5% | 89.5% | 89.1% | 91.5% | 94.1% |
| Percent Pore Volume in Pores Greater than 1 Micron[c] | 87.0% | 82.5% | 83.4% | 82.3% | 83.5% | 61.0% |
| % Wt. Alpha Alumina | 99.5 | 98 | 98.5 | 98.5 | 98 | 70–75 |
| Water Leachable Na, ppmw | 12 | 53 | 21 | 24 | 18 | No Data |
| Acid-Leachable Na, ppmw | 40 | 96 | 87 | 51 | 45 | No Data |
| Water-Leachable K, ppmw | 5 | 22 | 21 | 22 | 10 | No Data |
| Acid-Leachable Fe, ppmw | 2 | 5 | No Data | 1 | 5 | No Data |
| % Wt. SiO$_2$ | .5 | 2 | 1.5 | 15 | 2 | 25–30 |

[a] Method of Brunauer, Emmet and Teller, loc. cit.
[b] Flat Plate Crush Strength, single pellet.
[c] Determined by mercury intrusion to 55,000 psia using Micrometrics Autopore 9200 or 9210 (130° Contact angle, 0.473 N/m surface tension of Hg).
[e] Median pore diameter represents the pore diameter wherein 50% of the total pore volume is found in pores having less than (or greater than) the median pore diameter.

Regardless of the character of the support or carrier used, it is preferably shaped into particles, chunks, pieces, pellets, rings, spheres, wagon wheels, and the like of a size suitable for employment in fixed bed reactors. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15–45 feet long filled with catalyst. In such reactors, it is desirable to employ a support formed into a rounded shape, such as, for example, spheres, pellets, rings, tablets and the like, having diameters from about 0.1 inch to about 0.8 inch.

As with any supported catalyst, the optimal performance will depend upon optimizing the carrier in terms of its chemical composition/including impurities), surface area, porosity and pore volume. However, the enhancement in performance provided by this invention may be most pronounced when using less than optimized carriers. Thus, in demonstrating the invention in the examples, a variety of carriers are used.

The catalysts of this invention preferably contain, in addition to the manganese component, at least one other promoter or modifier to enhance the performance of the catalyst, e.g., to enhance efficiency or reduce the burning of ethylene oxide or affect activity. These promoters or modifiers are generally provided as chemical compounds.

For the sake of ease of understanding, the promoters will be referred to in terms of cation promoters, e.g., alkali and alkaline earth metals, and anion promoters. Compounds Such as alkali metal oxide or $MoO_3$, while not being ionic, may convert to ionic compounds, e.g., during catalyst preparation or in use. Whether or not such a conversion occurs, they will be referred to herein in terms of cation and anion species, e.g., alkali metal or molybdate.

Frequently, the catalyst contains alkali metal and/or alkaline earth metal as cationic promoter. Exemplary of the alkali metal and/or alkaline earth metals are lithium, sodium, potassium, rubidium, cesium, beryllium, magnesium, calcium, strontium and barium. Other cationic promoters include Group 3b metal ions including scandium, yttrium, lanthanum and the lanthanide series metals. In some instances, the promoter comprises a mixture of cations, e.g., cesium and at least one other alkali metal, to obtain a synergistic efficiency enhancement as described in British Patent No. 2,043,481 discussed above. The cation promoter may, of course, provide the counter ion to a manganate anion Component. Cesium salts alone or in combination with other salts are often used.

In many instances, the catalyst preferably comprises salt(s) of at least one oxyanion of an element (other than oxygen) having an atomic number of 5 to 83 and being from groups 3b to 7b or groups 3a to 7a, inclusive, of the Periodic Table. In some instances, it has been found beneficial to add more anion than is required to associate with the total alkali metal and alkaline earth metal being provided to the catalyst. The reason why such additional anion is beneficial in these situations is not known. The additional anion may be added in the form of an acid, an ammonium salt, an amine salt, etc., or a portion of the alkali metal and/or alkaline earth metal may be added as an acid salt, e.g., cesium hydrogen sulfate.

The concentration of the salt(s) (including any other alkali metal and alkaline earth metal salts) in the finished catalyst is not narrowly critical and may vary over a wide range. The optimum salt concentration for a particular catalyst will be dependent upon performance characteristics, such as, catalyst efficiency, rate of catalyst aging and reaction temperature.

The concentration of salt (based on the weight of the cation, e.g., cesium) in the finished catalyst may vary from about 0.0005 to 1.0 weight percent, preferably from about 0.005 to 0.1 weight percent. The preferred amount of cation promoter deposited on or present on the surface of the carrier or catalyst generally lies between about 10 and about 4000, preferably about 15 and about 3000 and more preferably between about 20 and about 2500 ppm by weight of cation calculated on the total carrier material. Amounts between about 50 and about 2000 ppm are frequently most preferable. When cesium is used in mixture with other cations, the ratio of cesium salt to any other alkali metal and alkaline earth metal salt(s), if used, to achieve desired performance is not narrowly critical and may vary over a wide range. The ratio of cesium salt to the other salt(s) may vary from about 0.0001:1 to 10,000:1, preferably from about 0.001:1 to 1,000:1. Preferably, cesium comprises at least about 10, more preferably, about 20 to 100, percent (weight) of the total added alkali metal and alkaline earth metal in the finished catalyst.

In some preferred embodiments of this invention especially when using other than a redox pair catalyst, the amount of leachable potassium cation as determined by leaching in a mineral acid, particularly nitric acid in a concentration of about 10 percent by volume at a temperature of about 90° C. for about 1 hour followed by washing with distilled water, is less than about 50, preferably less than about 25, e.g., 0 to 25, ppmw based on the weight of the catalyst. In some instances, the low level of leachable potassium appears, in combination with the manganese component, to enhance or to permit the manganese component to achieve greater enhancement of the activity and/or stability of the catalyst. Also, in many instances, preferred embodiments of the catalysts of this invention contain less than about 100, e.g., less than about 50, ppmw of leachable sodium cation as determined by the above procedure.

The types of anion promoters or modifiers suitable for use in the catalysts of this invention comprise, by way of example only, oxyanions such as sulfate, $SO_4^{-2}$, phosphates, e.g., $PO_4^{-3}$, titanates, e.g. $TiO_3^{-2}$, tantalates, e.g., $Ta_2O_6^{-2}$, molybdates, e.g., $MoO_4^{-2}$, vanadates, e.g., $V_2O_4^{-2}$, chromates, e.g. $CrO_4^{-2}$, zirconates, e.g., $ZrO_3^{-2}$, polyphosphates, nitrates, chlorates, bromates, borates, silicates, carbonates, tungstates, thiosulfates, cerates and the like. Halide ions may also be present as anions and include fluoride, chloride, bromide and iodide.

It is well recognized that many anions have complex chemistries and may exist in one or more forms, e.g., orthovanadate and metavanadate; and the various molybdate oxyanions such as $MoO_4^{-2}$, $Mo_7O_{24}^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. Preferably, the element is associated with oxygen, i.e., is an oxyanion, a covalent oxide or has an oxygen-containing anion. In many instances, analytical techniques may not be sufficient to precisely identify the species present. The invention is not intended to be limited by the exact species that may ultimately exist on the catalyst during use but rather reference herein to oxyanions is intended to provide guidance to understanding and practicing the invention.

A particularly preferred anion promoter includes the sulfates and oxyanions of rhenium, molybdenum, tungsten and/or chromium. Examples of anions of sulfur that can be suitably applied include sulfate, sulfite, bisulfite, bisulfate, sulfonate, persulfate, thiosulfate, dithionate, dithionite, halosulfate, e.g., fluorosulfate, etc. Preferred compounds to be applied are ammonium sulfate and the alkali metal sulfates. Examples of anions of molybdenum, tungsten and chromium that can be suitably applied include molybdate, dimolybdate, paramolybdate, other iso- and heteropolymolybdates, etc.; tungstate, paratungstate, metatungstate, other iso- and hetero- polytungstates, etc.; and chromate, dichromate, chromite, halochromate, etc. Preferred are sulfates, molybdates, tungstates and chromates.

When the catalyst comprises rhenium, the rhenium component can be provided in various forms, e.g., as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, i.e., $ReO_4$. Similar chemistries can be exhibited by other metals such as molybdenum and tungsten.

The amount of anion promoter may vary widely, e.g., from about 0.0005 to 2 weight percent, preferably from about 0.001 to 0.5 weight percent based on the total weight of the catalyst. When used, the rhenium component is often provided in an amount of at least about 1, say, at least about 5, e.g., about 10 to 2000, of ten between 20 and 1000, ppmw calculated as the weight of rhenium based on the total weight of the catalyst.

The catalysts of this invention may be of the type comprising at least one efficiency-enhancing salt of a member of a redox-half reaction pair which are intended to be employed in epoxidation processes in which at least one efficiency-enhancing gaseous member of a redox-half reaction pair is present (described hereinbelow). The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213–1218 (1961) or "CRC Handbook of Chemistry and Physics", 65th Edition, CRC Press, Inc., Boca Raton, Fla., pages D155–162 (1984). The term "redox-half reactions pair" refers to the pairs of atoms, molecules or ions or mixtures thereof which undergo oxidation or reduction in such half-reaction equations. Such terms as redox-half reaction pairs are used herein to include those members of the class of substance which provide the desired performance enhancement, rather than a mechanism of the chemistry occurring. Preferably, such compounds, when associated with the catalyst as salts of members of a half reaction pair, are salts in which the anions are oxyanions, preferably an oxyanion of a polyvalent atom; that is, the atom of the anion to which oxygen is bonded is capable of existing, when bonded to a dissimilar atom, in different valence states. Potassium is the preferred cation, although sodium, rubidium and cesium may also be operable, and the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred.

The salt of a member of a redox-half reaction pair is added in an amount sufficient to enhance the efficiency of the epoxidation reaction. The precise amount will vary depending upon such variables as the gaseous efficiency-enhancing member of a redox-half reaction used and concentration thereof, the concentration of other components in the gas phase, the amount of silver contained in the catalyst, the surface area of the, support, the process conditions, e.g., space-velocity and temperature, and morphology of support. Generally, however, a suitable range of concentration of the added efficiency-enhancing salt, calculated as cation, is about 0.01 to about 5 percent, preferably about 0.02 to about 3 percent, by weight, based on the total weight of the catalyst. Most preferably the salt is added in an amount of about 0.03 to about 2 weight percent.

In any event, the cation and/or anion promoters are provided in a promoting amount. As used herein the term "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), selectivity, activity, conversion, stability and yield. It is understood by one skilled in the art that one or more of the individual catalytic properties may be enhanced by the "promoting amount" while other catalytic properties may or may not be enhanced or may even be diminished. Indeed, the promoter may enhance efficiency but decrease activity of the catalyst as determined under standard Ethylene Oxide Process Conditions. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

A variety of procedures may be employed for preparing catalysts in accordance with the present invention. The preferred procedure comprises: (1) impregnating a porous catalyst carrier with a solution comprising a solvent or solubilizing agent, silver complex in an amount sufficient to deposit the desired weight of silver and the aforementioned anion and/or cation promoters upon the carrier, and (2) thereafter treating the impregnated support to convert the silver salt to silver metal and effect deposition of silver and the anion and/or cation promoters onto the exterior and interior surfaces of the support.

For sake of repeatability, in the use and reuse of impregnating solutions the carrier should preferably not contain undue amounts of ions which are soluble in the impregnating solution and/or exchangeable with the promoter supplied to the catalyst, either in the preparation or use of the catalyst, so as to upset the amount of promoter which provides the desired catalyst enhancement. If the carrier contains such ions, the ions should generally be removed by standard chemical techniques such as leaching. Silver and promoter depositions are generally accomplished by heating the carrier at elevated temperatures to evaporate the liquid within the support and effect deposition of the silver and promoters onto the interior and exterior carrier surfaces. Impregnation of the carrier is the preferred technique for silver deposition because it utilizes silver more efficiently than coating procedures, the latter being generally unable to effect substantial silver deposition onto the interior surface of the carrier. In addition, coated catalysts are more susceptible to silver loss by mechanical abrasion.

The sequence of impregnating or depositing the surfaces of the carrier with silver and promoters is optional. Thus, impregnation and deposition of silver and salts may be effected coincidentally or sequentially, i.e., the promoters may be deposited prior to, during, or subsequent to silver addition to the carrier. The promoters may be deposited together or sequentially. For example, one or more of the salts may be deposited first followed by the coincidental or sequential deposition of silver and additional or other salts.

Impregnation of the catalyst carrier is effected using one or more solutions containing silver and promoters in accordance with well-known procedures for coincidental or sequential depositions. For coincidental deposition, following impregnation the impregnated carrier is heat or chemically treated to reduce the silver compound to silver metal and deposit the salts onto the catalyst surfaces.

For sequential deposition, the carrier is initially impregnated with silver or promoter (depending upon the sequence employed) and then heat or chemically treated as described above. This is followed by a second impregnation step and a corresponding heat or chemical treatment to produce the finished catalyst containing silver and promoters.

In making the catalysts of this invention, some promoters such as some alkali and alkaline earth metal salts have such high melting temperatures that when deposited on the support with silver compound, and subjected to heating to convert the silver compound to silver metal, the salts may remain essentially unchanged. Of course, it is realized that alkali metal and alkaline earth metal salts having an unstable oxidation state will change to a stable oxidation state or states, e.g., sulfites to sulfates. When, for instance, the alkali metal or alkaline earth metal is deposited as the hydroxide or carbonate, it may be transformed in the presence of amines, which may be used in the impregnation of the catalyst, to a different salt form (i.e., nitrate) during the heating (roasting) step depending on the roast conditions.

The silver solution used to impregnate the carrier is comprised of a silver compound in a solvent or complexing/solubilizing agent such as the silver solutions disclosed in the art. The particular silver compound employed may be chosen, for example, from among silver complexes, nitrate, silver oxide or silver carboxylates, such as silver acetate, oxalate, citrate, phthalate, lactate, propionate, butyrate and higher fatty acid salts. Desirably, silver oxide complexed with amines is the preferred form of silver in the practice of the invention.

A wide variety of solvents or complexing/solubilizing agents may be employed to solubilize silver to the desired concentration in the impregnating medium. Among those disclosed in the art as being suitable for this purpose are lactic acid (U.S. Pat. Nos. 2,477,436 to Aries; and 3,501,417 to DeMaio); ammonia (U.S. Pat. No. 2,463,228 to West, et al.); alcohols, such as ethylene glycol (U.S. Pat. Nos. 2,825,701 to Endler, et al.,; and 3,563,914 to Wattimina); and amines and aqueous mixtures of amines (U.S. Pat. Nos. 2,459,896 to Schwarz; 3,563,914 to Wattimina; 3,215,750 to Benisi; 3,702,259 to Nielsen; and 4,097,414, 4,374,260 and 4,321,206 to Cavitt).

A particularly preferred process for making high silver content catalysts involves two or more sequential impregnations of silver, with or without promoters, each of which impregnations may be followed by roasting or other procedure to render the silver insoluble. Advantageously, the carrier has a high pore volume and surface area when using high silver loadings.

Following impregnation of the catalyst carrier with silver and promoter, the impregnated carrier particles are separated from any remaining non-absorbed solution. This is conveniently accomplished by draining the excess impregnating medium or, alternatively, by using separation techniques, such as filtration or centrifugation. The impregnated carrier is then generally heat treated (e.g., roasted) to effect decomposition and reduction of the silver metal compound (complexes in most cases) to metallic silver and the deposition of alkali metal and alkaline earth metal salts. Such roasting may be carried out at a temperature of from about 100° C. to 900° C., preferably from 200° to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support, (e.g., U.S. Pat. No. 3,563,914 suggests heating for less than 300 seconds to dry, but not roast to reduce, the catalyst; U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range), it is only important that the reduction time be correlated with temperature such that substantially complete reduction of the silver salt to metal is accomplished. A continuous or step-wise heating program is desirably used for this purpose. Continuous roasting of the catalyst for a short period of time, such as for not longer than ½ hour is preferred and can be effectively done in making the catalysts of this invention.

Heat treatment is preferably carried out in air, but a nitrogen or carbon dioxide atmosphere may also be employed. The equipment used for such heat treatment may use a static or flowing atmosphere of such gases to effect reduction, but a flowing atmosphere is much preferred.

An important consideration in making the catalyst of this invention is to avoid the use of strongly acidic or basic solutions which can attack the support and deposit impurities which can adversely affect the performance of the catalyst. The preferred impregnation procedure of U.K. Patent 2,043,481 coupled with the high roasting temperature, short residence time procedure which the patent also described is especially beneficial in minimizing such catalyst contamination. However, the use of the salts of this invention coupled with the high purity supports allows one to use lower temperatures though short residence times are preferred.

The particle size of silver metal deposited upon the carrier is asserted by a portion of the prior art to be a function of the catalyst preparation procedure employed. This may seem to be the case because of the limited ability of the art to effectively view the surface of the catalyst. Thus the space between the silver particles seen on the carrier has not been characterized sufficiently to say whether such particles of silver represent all the silver on the carrier. However, the particular choice of solvent and/or complexing agent, silver compound, heat treatment conditions and catalyst carrier may affect, to varying degrees, the range of the size of the resulting silver particles seen on the carrier. For carriers of general interest for the production of ethylene oxide, a distribution of silver particle sizes in the range of 0.005 to 2.0 microns is typically obtained. However, the role of particle size of the silver catalyst upon the effectiveness of the catalyst in making ethylene ozide is not clearly understood. In view of the fact that the silver particles are known to migrate on the surface of the catalyst when used in the catalytic reaction resulting in a marked change in their size and shape while the catalyst is still highly effective suggests that the silver particle size viewed on the support may not be a significant factor in catalytic performance.

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as temperature, pressure, residence time, concentration of reactants, gas phase diluents (e.g., nitrogen, methane and $CO_2$), gas phase inhibitors (e.g., ethylene chloride and ethylene dichloride), and the like.

The gases fed to the reactor may contain modifiers or inhibitors or additives such as disclosed by Law, et al., in U.S. Pat. Nos. 2,279,469 and 2,279,470, such as nitrogen oxides and nitrogen oxides generating compounds. See also, European Patent No. 3642. Especially European Patent No. 3642 employ catalysts comprising at least one efficiency-enhancing salt of a redox-half reaction pair in conjunction with at least one gaseous efficiency-enhancing member of a redox-half reaction pair.

The terms "gaseous member of a redox-half reaction pair", "gaseous efficiency-enhancing member of a redox-half reaction pair", or like terms referred to herein have a meaning similar to that for the "salt of a member of a redox-half reaction pair" or like terms, defined above. That is, these terms refer to members of half-reactions, represented in standard or single electrode potential tables in standard reference texts or handbooks which are in a gaseous state and are substances which, in the reaction equations represented in the texts, are either oxidized reduced. The preferred gaseous efficiency-enhancing materials are compounds containing an element capable of existing in more than two valence states, preferably nitrogen and another element which is, preferably, oxygen. Examples of preferred gaseous efficiency-enhancing members of redox-half reaction pairs include at least one of NO, $NO_2$, $N_2O_4$, $N_2O_3$ or any gaseous substance capable of forming one of the aforementioned gases, particularly NO and $NO_2$, under epoxidation conditions, and mixtures thereof with one or more of $PH_3$, CO, $SO_3$, $SO_2$, $P_2O_5$, and $P_2O_3$. NO is often preferred as the gaseous efficiency-enhancing compound.

Although in some cases it is preferred to employ members of the same half-reaction pair in the reaction system, i.e., both the efficiency-enhancing salt member associated with the catalyst and the gaseous member in the feedstream, as, for example, with a preferred combination of potassium nitrate and nitric oxide, this is not necessary in all cases to achieve satisfactory results. Other combinations, such as $KNO_3/N_2O_3$, $KNO_3/NO_2$, $KNO_3/N_2O_4$, $KNO_3/SO_2$, $KNO_2/NO$, $KNO_2/NO_2$ and $KNO_3$/a mixture of $SO_2$ and NO, may also be employed in the same system. In some instances, the salt and gaseous members may be found in different half-reactions which represent the first and last reactions in a series of half-reaction equations of an overall reaction.

The gaseous efficiency-enhancing member of a redox-half reaction pair is also present in an amount sufficient to enhance the performance, such as the activity of the catalyst, and, particularly, the efficiency of the epoxidation reaction. The precise amount is determined, in part, by the particular efficiency-enhancing salt of a member of a redox-half reaction pair used and the concentration thereof, the particular alkene undergoing oxidation, and by other factors noted above which influence the amount of efficiency-enhancing salt of a member of a redox-half reaction pair. Typically a suitable concentration of the gaseous member of a redox-half reaction pair for epoxidation of most alkenes, including propylene, is about 0.1 to about 2,000 ppm, by volume, of the gaseous feedstream when $N_2$ is used as ballast. When a preferred gaseous member of a redox-half reaction pair, such as NO, is used in the epoxidation of propylene, the preferred concentration is about 2,000 ppm, by volume, with an $N_2$ ballast. However, when ethylene is being oxidized, a suitable concentration for ethylene is from about 0.1 to about 100 ppm, by volume, of the gaseous feedstream components. Preferably, the gaseous efficiency-enhancing member of a redox-half reaction pair is present in an amount of about 1 to about 80 ppm when about 3 percent, by volume, $CO_2$ is present in the reaction mixture. When nitric oxide is employed as the gaseous efficiency-enhancing compound in an ethylene epoxidation system, it is present in an amount of about 0.1 to about 60 ppm, preferably about 1 to about 40 ppm, when $CO_2$ is present in the reaction mixture, e.g., in amounts up to about 3 volume percent.

The desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the commercially-practiced processes are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large-scale reactors are generally on the order of about 0.1–5 seconds. Oxygen may be supplied to the reaction in an oxygen-containing stream, such as air or as commercial oxygen. The resulting ethylene oxide is separated and recovered from the reaction products using conventional methods. However, for this invention, the ethylene oxide process envisions the normal gas recycle encompassing carbon dioxide recycle in the normal concentrations, e.g., about 0.5 to 6 volume percent.

The specific STANDARD ETHYLENE OXIDE PROCESS CONDITIONS are used in the examples below unless indicated otherwise. In commercial processes, typical operating conditions can vary and the amounts of the ingredients employed can be adjusted to achieve the best efficiencies. In particular the amounts of ethane, carbon dioxide and organic chloride can be varied to optimize efficiency for the manufacture of ethylene oxide. Ethane is an impurity contained in varying amounts in ethylene raw material. Ethane can also be added to a commercial reactor to provide better control of the chloride's inhibitor action. Typically, the amount of ethane used in commercial processes can vary from about 0.001 to about 5 mole percent for achieving optimization under both air process conditions and oxygen process conditions. As the concentration of ethane increases in the reactor, the effective surface chloride concentration on the catalyst is believed to be decreased thereby decreasing the ability of chloride to promote/inhibit reactions that increase efficiency for the manufacture of ethylene oxide. The amount of chloride, e.g., ethyl chloride or ethylene dichloride, can be varied to provide the needed promoter/inhibitor action commensurate with the ethane levels encountered in a particular process and the type of promoters or modifiers used in the catalyst. The amount of organic chloride used in commercial processes can typically vary from about 1.0 ppm to about 100 ppm for achieving optimization under both air process conditions and oxygen process conditions. Carbon dioxide is generally considered an inhibitor, and the inhibitor effect of carbon dioxide on process efficiency may be variable with its concentration. With different types of promoters or modifiers used in preparation of the catalysts of this invention, different concentrations of carbon dioxide may be more desirable in certain commercial processes. Typically, the amount of carbon dioxide used in commercial processes can vary from about 2 to about 15 mole percent for achieving optimization under both air process conditions and oxygen process conditions. The amount of carbon dioxide is dependent on the size and type of carbon dioxide scrubbing system employed. The optimization of the amounts of ethane, carbon dioxide and organic chloride provides catalysts which are especially suitable for obtaining desired efficiencies in commercial ethylene oxide manufacture. Especially in the epoxidation processes using at least one gaseous efficiency-enhancing member of a redox-half reaction pair in conjunction with at least one salt of a member of a redox-half reaction pair on the catalyst, the concentration of carbon dioxide is preferably maintained below about 1.5, e.g., below about 1.0 or even about 0.5, volume percent.

Catalysts which have been subjected to process conditions for ethylene oxide manufacture such as STANDARD ETHYLENE OXIDE PROCESS CONDITIONS are considered an important aspect of this invention.

EXAMPLES

The following detailed procedures are provided as illustrative of methods and carriers which are useful for preparing catalysts according to the invention. These examples are by way of illustration only and are not to be construed as limiting the scope of the invention described herein.

The carrier, as indicated, is impregnated under vacuum as hereinafter described with a solution of silver complex and alkali metal and alkaline earth metal salts. The alkali metal and/or alkaline earth metal-containing components need not be introduced as the salts. For instance, cesium hydroxide may be used in conjunction with an ammonium salt (e.g., ammonium sulfate) or acid (e.g., sulfuric acid) or organic compound (e.g., ethylsulfonate) and under conditions of catalyst preparation or use, conversion is made to the desired species. The impregnating solution is prepared at a concentration such that the finished catalyst contained the desired amounts of silver and promoter or modifier. The required concentration of silver and promoter in solution for the given carrier is calculated from the packing density (grams/cc) and pore volume Of the carrier which are either known or readily determined. The relationship can vary depending upon the nature of the carrier, e.g., pore volume may influence the amount of silver deposited from a given solution. The required concentration of promoter in solution is obtained by dividing the solution silver concentration by the ratio of silver to promoter desired in the finished catalyst.

In preparing the catalysts, generally a desired amount of ethylenediamine (high purity grade) is mixed with indicated amounts of distilled water. Then oxalic acid dihydrate (reagent grade) is then added slowly to the solution at ambient temperature (23° C.) while continuously stirring. During this addition of oxalic acid, the solution temperature typically rises to about 40° C. due to the reaction exotherm. Silver oxide powder (Metz Corporation) is then added to the diamine-oxalic acid salt-water solution while maintaining the solution temperature below about 40° C. Finally, monoethanolamine, aqueous alkali metal salt solution(s) and distilled water are added to complete the solution. The specific gravity of the resulting solution is often about 1.3–1.4 g/ml.

Carrier can be impregnated in a 12 inches long by 2 inches I.D. glass cylindrical vessel equipped with a suitable stopcock for draining the carrier after impregnation, however, other suitable flask sizes and types can be used. A suitable size separatory funnel for containing the impregnating solution is inserted through a rubber stopper equipped with a metal tube for attaching a vacuum line into the top of the impregnating vessel. The impregnating vessel containing the carrier is evacuated to approximately 2 inches of mercury pressure for about 20 minutes after which the impregnating solution is slowly added to the carrier by opening the stopcock between the separatory funnel and the impregnating vessel until the carrier is completely immersed in solution, the pressure within the vessel being maintained at approximately 2 inches of mercury. Following addition of the solution, the vessel is opened to the atmosphere to attain atmospheric pressure. The carrier then remains immersed in the impregnating solution at ambient conditions for about 1 hour, and thereafter is drained of excess solution for about 30 minutes. The impregnated carrier is then heat treated as follows (unless stated otherwise) to effect reduction of silver salt and deposition of promoter on the surface. The impregnated carrier is spread out in a single layer on a 2⅝ inches wide endless stainless steel belt (spiral weave) and transported through a 2 inches by 2 inches square heating zone for 2.5 minutes, the heating zone being maintained at 500° C. by passing hot air upward through the belt and about the catalyst particles at the rate of 266 SCFH. The hot air is generated by passing it through a 5 ft. long by 2 inches I.D. stainless steel pipe which was externally heated by an electric furnace (Lindberg (™) tubular furnace: 2½ inches I.D., 3 feet long heating zone) capable of delivering 5400 watts. The heated air in the pipe is discharged from a square 2 inches by 2 inches discharge port located immediately beneath the moving belt carrying the catalyst carrier. After being roasted in the heating zone, the finished catalyst is weighed, and based upon the weight gain of the carrier, and the known ratios of silver to promoter in the impregnating solution, it is calculated to contain the wt. % of silver, and wt. % promoter desired.

The analysis for silver is carried out by the following method: An approximately 50 g sample of catalyst is powdered in a mill and 10 g of the powdered sample weighed to the nearest 0.1 mg. The silver in the catalyst sample is dissolved in hot (80° C.), 50% by volume, nitric acid solution. The insoluble alumina particles are filtered and washed with distilled water to remove all adhering nitrate salts of Ag, Cs, etc. This solution is made up to 250 ml in a volumetric flask using distilled water. A 25 ml aliquot of this solution is titrated according to standard procedures using a 0.1 Normal solution of ammonium thiocyanate and ferric nitrate as indicator. The amount of Ag so determined in 250 ml solution is then used to calculate the weight percent silver in the catalyst sample.

Silver and promoter concentrations for all catalysts described in the specification are calculated values as described above.

Carriers are nominally ring shape having dimensions of about 1/8×5/16×5/16 inch or about 1/8×1/4×1/4 inch.

CARRIER "J"

Carrier J is an alpha-alumina carrier prepared by calcining gamma-alumina (N-6573) to a maximum temperature of about 1025° C. which had been impregnated with an aqueous 3.44 weight percent ammonium fluoride solution. The carrier contains at least 99.0 weight percent alpha-alumina, about 0.2 weight percent fluoride and as water leachable components:

| | |
|---|---|
| aluminum | 118 ppmw |
| calcium | 68 ppmw |
| magnesium | 7 ppmw |
| potassium | 3 ppmw |
| sodium | 36 ppmw |
| fluoride | 375 ppmw |
| nitrate | 4 ppmw |
| phosphate | 30 ppmw |
| fluorophosphate | 3 ppmw |
| sulfate | 2 ppmw |
| silicon | 6 ppmw |

| Physical Properties of Carrier "J" | |
|---|---|
| Surface Area | 1.09 m²/g |
| Pore Volume | 0.668 cc/g |
| Median Pore Diameter | 1.85 microns |
| Packing Density | 0.53 g/ml |

| Pore Size Distribution, % Total Pore Volume | |
|---|---|
| Pore Size Microns | % Total Pore Volume |
| $P_1$ (<0.1) | 0 |
| $P_2$ (0.1–0.5) | 1 |
| $P_3$ (0.5–1.0) | 6 |
| $P_4$ (1.0–10) | 88.5 |
| $P_5$ (10–100) | 1.5 |
| $P_6$ (>100) | 3 |

CARRIER "K"

Carrier K is Carrier J which had been washed five times with hot deionized water (approximately 70° C.).

CARRIER "N"

Chemical Composition of Carrier "N"
alpha-Alumina at least about 98 wt. %
Acid Leachable Impurities:
Leachate contained 378 ppm sodium and 330 ppm potassium.

| Physical Properties of Carrier "N" | |
|---|---|
| Surface Area (Kr) (1) | 1.166 m²/g |
| Pore Volume (2) | 0.697 cc/g |
| Packing Density (3) | 34.2 lbs/ft³ |
| Median Pore Diameter (4) | 15 microns |
| Apparent Porosity (%) | 72 |
| % Water Absorption | 65.4 |
| Bulk density | 1.1 g/cc |

CARRIER "O"

Carrier O is an alpha-alumina carrier prepared by calcining gamma-alumina (N-6573) impregnated with about 3.4 weight percent ammonium fluoride solution to a maximum temperature of about 1025° C. The chemical and physical properties of the carrier are given below:

| Chemical Composition of Carrier "O" | |
|---|---|
| alpha-Alumina | 99 wt. % |
| Fluoride | 0.28 wt. % |

Water Leachable Impurities:
64 ppm aluminum, 9 ppm calcium, 5 ppm magnesium, 2 ppm potassium, 12 ppm sodium, 2 ppm silicon, 173 ppm fluoride, 11 ppm nitrate, 3.2 ppm phosphate and 2 ppm sulfate.

| Physical Properties of Carrier "O" | |
|---|---|
| Surface Area (1) | 1.10 m²/g |
| Pore Volume (2) | 0.69 cc/g |
| Packing Density (3) | 52.38 g/ml |
| Median Pore Diameter (4) | 2.3 microns |

| Pore size Distribution, % Total Pore Volume (4) | |
|---|---|
| Pore Size Microns | % Total Pore Volume |
| $P_1$ (<0.1) | 0 |
| $P_2$ (0.1–0.5) | 1 |
| $P_3$ (0.5–1.0) | 5 |
| $P_4$ (1.0–10.0) | 89.2 |
| $P_5$ (10.0–100) | 1.8 |
| $P_6$ (>100) | 3 |

CARRIER "P"

Carrier "P" is a binderless alpha-alumina carrier.

| Chemical Composition of Carrier "P" | |
|---|---|
| alpha-Alumina | 99 wt. % |

Water Leachable Impurities:
168 ppm aluminum, 30 ppm calcium, 1.3 ppm magnesium, 102 ppm potassium, 197 ppm sodium, 148 1 ppm silicon, 0.8 ppm vanadium, 2.8 ppm phosphorus, 1 ppm chloride, 2 ppm nitrate, 5 ppm phosphate, ppm sulfate, 3 ppm fluoride, 4 ppm acetate, and 1 ppm formate.

| Physical Properties of Carrier "P" | |
|---|---|
| Surface area (1) | 1.35 m²/g |
| Pore Volume (2) | 0.561 cc/g |
| Median Pore Diameter (4) | 6.3 microns |
| Packing Density (3) | 0.61 g/ml |

| Pore Size Distribution, % Total Pore Volume (4) | |
|---|---|
| Pore Size Microns | % Total Pore Volume |
| $P_1$ (<0.1) | 0.5 |
| $P_2$ (0.1–0.5) | 16.0 |
| $P_3$ (0.5–1.0) | 17.0 |
| $P_4$ (1.0–10.0) | 18.5 |
| $P_5$ (10.0–100) | 38.5 |
| $P_6$ (l100) | 8.5 |

CARRIER "Q"

Carrier "Q" is prepared by soaking Carrier "P" in 10% HF solution at 25° C. for one hour and washing with deionized distilled water at 25° C. five times followed by drying in air at 300° C. for 1 hour.
Water Leachable Impurities:
266 ppm aluminum, 313 ppm calcium, 5.4 ppm magnesium, 128 ppm potassium, 106 ppm sodium, 16 ppm silicon, 0.2 ppm vanadium, 0.3 ppm zinc, 1.8 ppm phosphorus, 1 ppm chloride, 10 ppm nitrate, 1 ppm sulfate, and 1011 ppm fluoride.

CARRIER R

Carrier R is prepared by washing Carrier O five times with hot, deionized water (approximately 70° C.).

CARRIER S

Carrier S is an alpha-alumina carrier prepared by calcining a boehmite-ammonium bifluoride mixture containing 3 weight percent of ammonium bifluoride first at about 600° C. and calcining again at about 1025° C. The chemical and physical properties of the carrier are given below:

| Chemical Composition of Carrier S | |
|---|---|
| alpha-Alumina | 99 wt % |
| Fluoride | 0.25 wt % |

Water Leachable Impurities
6 ppm aluminum, 9 ppm calcium, 5 ppm magnesium, 1 ppm potassium, 13 ppm sodium, 36 ppm fluoride, 1 ppm sulfate.

| Physical Properties of Carrier S | |
|---|---|
| Surface Area | 1.24 m²/g |
| Pore Volume | 0.77 cc/g |
| Packing Density | 0.50 g/ml |
| Medium Pore Diameter | 1.7 microns |

| Pore Size Distribution, % Total Pore Volume | |
|---|---|
| Pore Size Microns | % Total Pore Volume |
| $P_1$ (<0.1) | 0.5 |
| $P_2$ (0.1–0.5) | 3 |
| $P_3$ (0.5–1.0) | 9.5 |
| $P_4$ (1.0–10) | 81 |
| $P_5$ (10–100) | 2 |
| $P_6$ (l100) | 4 |

CARRIER T

Carrier T is an alpha-alumina carrier prepared by calcining a boehmite-ammonium bifluoride mixture containing 3 weight percent of ammonium bifluoride first at about 600° C. and calcining again at about 1025° C. The chemical and physical properties of the carrier are given below:

| Chemical Composition of Carrier T | |
|---|---|
| alpha-Alumina | 99 wt % |
| Fluoride | 0.25 wt % |

Water Leachable Impurities
8 ppm aluminum, 17 ppm calcium, 8 ppm magnesium, 5 ppm potassium, 6 ppm sodium, 55 ppm fluoride, 1 ppm sulfate.

| Physical Properties of Carrier T | |
|---|---|
| Surface Area | 1.13 m²/g |
| Pore Volume | 0.75 cc/g |
| Packing Density | 0.51 g/ml |
| Medium Pore Diameter | 2.1 microns |

| Pore Size Distribution, % Total Pore Volume | |
|---|---|
| Pore Size Microns | % Total Pore Volume |
| $P_1$ (<0.1) | 0 |
| $P_2$ (0.1–0.5) | 1 |
| $P_3$ (0.5–1.0) | 4.5 |
| $P_4$ (1.0–10) | 90.5 |
| $P_5$ (10–100) | 1.5 |
| $P_6$ (l100) | 2.5 |

CARRIER U

Carrier U is Carrier T which had been washed five times with hot deionized water (approximately 70° C.).

(1) Method of Measurement described in "Adsorption Surface Area and Porosity", S. J. Gregg and K. S. W. Sing, *Academic Press* (1967), pages 316–321.

(2) Method of Measurement as described in ASTM C20–46.

(3) Calculated value based on conventional measurement of the weight of the carrier in a known volume container.

(4) Method of Measurement described in "Application of Mercury Penetration to Materials Analysis", C. Orr, Jr., *Powder Technology*, Vol. 3, pp. 117–123 (1970).

Attrition Loss and Crush Strength Average and Range are determined according to Test No. 45 and Test No. 6, respectively, as referred to in Catalyst Carriers Norton Company, Akron, Ohio Bulletin CC-11, 1974. 25 Ft. Drop Test is determined by dropping carrier pills through a tube for a vertical distance of 25 feet onto a steel plate and observing for breakage. Non-breakage of carrier pills indicates percent passing. Acid Leachable Impurities are determined by contacting carrier pills with 10% nitric acid for one hour at about 90° C. and determining extracted cations by standard Atomic Absorption spectroscopy techniques. Inductively Coupled Plasma Spectroscopy techniques may also be used for such determinations The identity and amounts of water leachable components of carriers can be determined by any convenient analytical technique. Generally, the carriers are heated in distilled water at a temperature of about 50° to 95° C., often 90° C., for about 0.5 to 2, e.g., 1 hour. The liquid is then subjected to ion chromatography and Inductively Coupled Plasma Spectroscopy techniques.

EXAMPLES 1 and 2

Example 1 is comparative. Table II below summarizes the details about the catalyst and the efficiencies at CONDITIONS. It should be appreciated that the catalyst performance characterized in these examples were not reflective of optimization of catalyst formulation.

The catalysts are prepared using the general procedures set forth below.

Impregnation Solution Preparation

1. Ethylenediamine (high purity grade) is mixed with distilled water.

2. Oxalic acid (oxalic acid dihydrate, reagent grade) is slowly added to the aqueous ethylenediamine solution at ambient Conditions. An exothermic reaction occurs and the solution temperature rises to about 40° C.

3. Silver oxide (powder from Metz) is then added slowly to the solution of step 2, 4. To the solution in 3 above is added the monoethanolamine (Fe and Cl free), (Note: Steps 1 to 4 were performed in a batch 3 times the size set forth herein and then divided into three aliquots, one of which was used for the subsequent steps).

5. The alkali metal salts are then added,

6. Distilled water is added to adjust the solution volume to 150 ml.

Impregnation Of Carrier

1. The carrier is evacuated at room temperature and the impregnation solution A above is added to the carrier under vacuum.

2. The excess solution is drained off.

Catalyst Roasting

1. The impregnation carrier is roasted in hot air using a belt roaster at about 500° C. for 2.5 minutes over a belt roaster, Air flow is 66 SCFH/in$_2$.

The catalysts are tested at STANDARD ETHYLENE OXIDE PROCESS CONDITIONS under oxygen conditions.

A summary of Examples 1 and 2 is provided in Table II.

solution is prepared by adding cesium sulfate to distilled water.

The standard solutions are added to the silver oxide-containing solution to provide the sought impregnating solution. The cesium perrhenate solution is heated to 75° C. to assure that the salt is dissolved, and the impregnating solution is warmed to about 40° C. to assure that the cesium perrhenate is dissolved.

Ten grams of support are added to a Pyrex impregnating chamber. The pressure of the chamber is reduced to about 2.0–5.0 mm Hg. The impregnating solution is slowly added to the chamber. The pressure of the chamber is allowed to rise back to atmospheric. The impregnating solution is drained after 20 minutes. The drained solution is retained in a covered beaker. The impregnated support is calcined in a roaster at 500° C. for 3 minutes. The impregnating and calcining steps are repeated using the drained solution for impregnation.

Table III summarizes the catalysts.

TABLE III

| Example No. | Silver wt % | Cs, ppm | Anion | Carrier |
|---|---|---|---|---|
| 3 | 30* | 395 | ReO$_4$ | N |
|   |     | 592 | SO$_4$  |   |
| 4 | 30* | 390 | ReO$_4$ | N |
|   |     | 592 | SO$_4$  |   |
|   |     | 160 | MnO$_4$ |   |
| 5 | 30* | 396 | ReO$_4$ | N |
|   |     | 594 | So$_4$  |   |
|   |     | 330 | MnO$_4$ |   |

TABLE II

| Example No. | Silver wt. % | Cs, ppm | Anion | Other Cation Metal | Other Cation Metal ppm | Other Anion Additive | Other Anion, ppm | Carrier | Efficiency % | Temp °C. |
|---|---|---|---|---|---|---|---|---|---|---|
| 1$^a$ (Comparative) | 31* | 60 | Cs$_2$Ta$_2$O$_6$$^2$ | — | — | — | — | K | 82.6 | 241 |
|  |  | 140 | Cs$_2$MoO$_4$ |  |  |  |  |  |  |  |
|  |  | 750 | Cs$_2$SO$_4$ |  |  |  |  |  |  |  |
| 2$^b$ | 30* | 220 | CsMnO$_4$ | — | — | — | — | K | 81.5 | 229 |
|  |  | 100 | Cs$_2$MoO$_4$ |  |  |  |  |  |  |  |
|  |  | 750 | Cs$_2$SO$_4$ |  |  |  |  |  |  |  |

$^a$. 2.0 ppm ethyl chloride, 6.0% inlet carbon dioxide.
$^b$. 2.0 ppm ethyl chloride, 6.0% inlet carbon dioxide.
*applied using two impregnation and calcination steps.

EXAMPLES 3 to 5

The following general procedure is used to prepare catalysts 3 to 5.

To a 100 ml Pyrex beaker with constant stirring are added:

7.5 grams ethylenediamine, 7.0 ml water, 7.51 grams oxalic acid, 13.16 grams silver oxide, and 2.63 grams monoethanolamine.

The beaker is covered with a watch glass between additions. The temperature of the solution after each addition ranges from 25° C. to 60° C. This mixture is then diluted with distilled water to 35 milliliters.

A cesium perrhenate standard solution containing 0.00531 grams of cesium per gram of solution is prepared by adding an equimolar amount of cesium hydroxide and ammonium perrhenate to distilled water. A cesium sulfate standard solution containing 0.015 grams of cesium per gram of The catalysts from Examples 3, 4 and 5 are used in a microreactor to evaluate performance. For the microreactor test, catalyst pills are crushed with a mortar and pestle and screened to the desired size (30–70 mesh). Two grams of crushed catalyst are loaded into a ¼ inch diameter by 5½ inch long stainless steel tube. The tube is placed inside a test oven and connected to a gas feed system. The temperature of the oven is controlled by a temperature controller and the reactor outlet pressure is controlled at 150 psig by a Groves back pressure regulator. The gas flow rate is adjusted to the desired gas hourly space velocity (12 liters per hour at standard temperature and pressure). The reaction temperature is measured with two thermocouples inside the reactor. One is immersed in the catalyst bed, about two inches down from the top of the reactor, and the other is located at the reactor outlet. The average of the two readings is recorded as the reaction temperature. The feed composition comprises 30 volume percent ethylene, 8 volume percent oxygen, 6.5 volume percent carbon dioxide, ethane and chlorides as noted in Table IV, and nitrogen as the balance of the gas.

TABLE IV

| Day | Catalyst 3 | | | Catalyst 4 | | | Catalyst 5 | | | Ethane, % | Ethyl chloride, ppm |
|---|---|---|---|---|---|---|---|---|---|---|---|
| | ΔEO % | Efficiency % | Temp °C. | ΔEO % | Efficiency % | Temp °C. | ΔEO % | Efficiency % | Temp °C. | | |
| 1 | 1.0 | 87.9/86.0[a] | 229 | 1.1 | 87.2 | 225 | 1.2 | 85.4 | 219 | 0.72 | 3.6 |
| 2 | — | — | — | 1.2 | 85.9 | 224 | 1.2 | 83.9 | 219 | 0.53 | 5.4 |
| 3 | 1.6 | 86.1 | 226 | 1.8 | 84.4 | 234 | 1.8 | 82.9 | 228 | 0.53 | 5.4 |
| 4 | 1.9 | 85.6 | 231 | 2.0 | 83.4 | 237 | 2.0 | 82.4 | 232 | 0.50 | 7.3 |
| 5 | 2.0 | 85.2 | 235 | 2.1 | 83.0 | 238 | 2.1 | 82.2 | 233 | 0.50 | 6.2 |
| 6 | 2.0 | 85.1 | 233 | 2.1 | 83.2 | 238 | 1.6 | 83.0 | 226 | 0.50 | 5.4 |
| 7 | 2.1 | 85.3 | 237 | 2.1 | 82.5 | 241 | 2.2 | 82.0 | 239 | 0.38 | 7.6 |
| 8 | 2.2 | 84.3 | 237 | 2.2 | 81.8 | 241 | 2.3 | 81.9 | 239 | 0.38 | 7.6 |
| 9 | 2.2 | 84.0 | 237 | 2.3 | 81.6 | 241 | 2.4 | 81.8 | 239 | 0.38 | 7.6 |
| 10 | 2.3 | 83.0 | 239 | 2.4 | 81.2 | 238 | 2.4 | 81.8 | 235 | 0.52 | 7.2 |
| 11 | 2.1 | 83.7 | 235 | 2.3 | 82.3 | 234 | 2.5 | 82.7 | 233 | 0.52 | 3.9 |
| 12 | 1.8 | 84.9 | 234 | 2.1 | 84.1 | 232 | 2.4 | 83.6 | 232 | 0.52 | 3.8 |

[a]poor mass balance

EXAMPLES 6 to 23

Catalysts 6 to 23 are prepared in a manner similar to that described in Examples 3 to 5. In each, the catalyst is prepared by a double impregnation technique as follows:

Carrier was impregnated with a solution containing the desired concentrations of silver salts and promoters using a cylindrical vessel equipped for impregnation under vacuum. The excess impregnating solution was drained from the vessel after the solution was contacted with the carrier for 30–60 minutes. The impregnated carrier was then roasted in a stream of air at 500° C. for 2.5 minutes. The described procedures were repeated once to give the final catalyst.

The silver weight loading and promoter levels of prepared catalyst depend on the concentration of the impregnation solution and the total pore volume of the carrier. For every mole of silver in solution, 1.05 moles ethylenediamine (EDA), 0.525 mole oxalic acid (OA), 0.378 mole monoethanolamine (MEA), and appropriate amounts of water and promoters are used. To prepare the impregnation solution, EDA is mixed with an appropriate amount of distilled water. Oxalic acid is then added slowly, while continuously stirring the solution at ambient conditions. However, the addition of OA being exothermic, the solution temperature may rise to about 40° C. The silver oxide and MEA are added next to the EDA-OA-water solution. Finally, promoter solution and balance water are added to give the desired silver and promoters concentrations.

To prepare a catalyst, carrier is evacuated at room temperature in the impregnating vessel. While the carrier is still under vacuum, the impregnating solution is introduced into the vessel and contacted with the carrier. The excess solution is drained from the vessel 30–60 minutes after the impregnation. The impregnated carrier is then spread in a monolayer fashion on a piece of stainless steel mesh and dried at 500° C. for 2.5 minutes in a stream of hot air at the rate of 244 SCFH in a 2"×2" hot zone. All catalysts are double-impregnated catalysts. Hence, the described procedures are repeated once using impregnating solution with desired concentration. The finished catalyst is weighed and from the weight gain of the carrier, the silver loading of the finished catalyst can be calculated. It is expected that some promoters added in the first impregnation may redissolve during the second impregnation. Therefore, the promoter concentration of the impregnation solution needs some adjustment to account for such loss in order to achieve the desired promoter level in the final catalyst.

Table V discloses the target content to be deposited in each of the components in each impregnation step and the final target content of the catalyst.

Table VI summarizes the performance of each of the catalysts in a miniautoclave reactor. The miniautoclave reactor is a 2-inch stainless steel internal recycle Betty reactor (available from Autoclave Engineers, Inc., Erie, Pa., U.S.A.). The reactor consists of a pressure vessel, a catalyst basket, an impeller, and a Magne-Drive assembly. The pressure vessel has a 2-inch inside diameter and provides the housing for the basket and the impeller. The catalyst basket is a stainless steel cylinder 1.25 inch in diameter and 1.06 inch in length. The bottom of the basket is constructed from a piece of stainless screen which provides a support for catalyst sample and still allows free passage of gas. Six stainless steel strips welded onto the side of the basket serve as baffles that guide the direction of gas flow inside the pressure vessel and as supports for the basket when the basket is inserted into the pressure vessel. The impeller is located above the basket and attached to the inner shaft of the Magne-Drive assembly. An inner shaft housing is attached onto the top of the pressure vessel and forms a closed space with the pressure vessel. The inner shaft is driven through magnetic force by external magnets, which are driven by an air or an electric motor. The rotation of the impeller, normally at 1500 rpm, forces the gas inside the pressure vessel to circulate through the catalyst basket. Reaction gas is fed into pressure vessel from the top and exits from the bottom. The temperature inside the vessel is controlled and is measured by a thermocouple inserted into the pressure vessel from the bottom. Catalysts are generally tested under the standard oxygen process conditions with 1.7–2 ppm ethyl chloride in a 2" backmixed autoclave at 275 psig. The catalyst test procedure used in the CONDITIONS involves the following steps:

1. About 8 cc of catalyst is charged to the backmixed autoclave. The volume of catalyst is calculated from the packing density of the carrier and the amount of silver and additives.

2. The backmixed autoclave is heated to about 230° C. in a nitrogen flow of 2 SCFH with the fan operating at 1500 rpm. The nitrogen flow is then discontinued and the epoxidation feed stream is introduced into the reactor. The total gas outlet flow is adjusted to about 2.2 SCFH (the flow is adjusted to provide the desired space velocity given the actual amount of catalyst charged). The temperature is gradually increased over the next 4 days so that the ethylene oxide concentration in the outlet gas is about 2%.

3. Catalyst is operated at constant temperature for about 1 to 4 weeks after the catalyst is fully activated. The activity aging rate is calculated from the changes of ethylene oxide concentration (mole %) at constant temperature operating conditions. Because efficiency of catalyst is a function of ethylene oxide concentration and ethylene oxide concentration normally does not remain constant during constant temperature test, the efficiency aging rate is calculated from the changes of an adjusted efficiency to account for the changes in ethylene oxide concentration. The adjusted efficiency at 2 mole % ethylene oxide is calculated by using the equation adjusted efficiency [%]=measured efficiency [%]+3.75 [%/mole %]×(measured ethylene oxide concentration [mole %]−2.0 [mole %]).

TABLE V

| Example | % Ag | ppm Cs (as $MnO_4^-$) | ppm Cs (as $MoO_4^=$) | ppm Cs (as $SO_4^=$) | Carrier |
|---|---|---|---|---|---|
| 6  | [1]8.9  | 16  | 62  | —   | —  |
|    | [2]22.1 | 20  | 80  | 750 | K  |
|    | [F]31.0 | 36  | 142 | 750 |    |
| 7  | [1]8.6  | 39  | 39  | —   | —  |
|    | [2]22.2 | 50  | 50  | 750 | K  |
|    | [F]30.8 | 89  | 89  | 750 |    |
| 8  | [1]8.5  | 62  | 15  | —   | —  |
|    | [2]22.6 | 80  | 20  | 750 | K  |
|    | [F]31.1 | 142 | 35  | 750 |    |
| 9  | [1]6.9  | 62  | 62  | —   | —  |
|    | [2]22.6 | 80  | 80  | 750 | K  |
|    | [F]29.5 | 142 | 142 | 750 |    |
| 10 | [1]8.2  | 40  | 88  | —   | —  |
|    | [2]20.2 | 50  | 110 | 750 | K  |
|    | [F]28.4 | 90  | 198 | 750 |    |
| 11 | [1]8.6  | 86  | 39  | —   | —  |
|    | [2]21.6 | 110 | 50  | 750 | K  |
|    | [F]30.2 | 196 | 89  | 750 |    |
| 12 | [1]8.6  | 158 | 63  | —   | —  |
|    | [2]21.1 | 200 | 80  | 750 | K  |
|    | [F]29.7 | 358 | 143 | 750 |    |
| 13 | [1]8.6  | 153 | 76  | —   | —  |
|    | [2]23.5 | 200 | 100 | —   | K  |
|    | [F]32.1 | 353 | 176 | —   |    |
| 14 | [1]7.2  | 132 | 39  | —   | —  |
|    | [2]22.2 | 170 | 50  | 750 | K  |
|    | [F]29.4 | 302 | 89  | 750 |    |
| 15 | [1]7.7  | 110 | 63  | —   | —  |
|    | [2]21.1 | 140 | 80  | 750 | K  |
|    | [F]28.8 | 250 | 143 | 750 |    |
| 16 | [1]7.8  | 132 | —   | —   | —  |
|    | [2]22.2 | 170 | —   | 750 | K  |
|    | [F]30   | 302 | —   | 750 |    |
| 17 | [1]8.0  | 180 | 39  | —   | —  |
|    | [2]21.8 | 230 | 50  | 750 | K  |
|    | [F]29.8 | 410 | 89  | 750 |    |
| 18 | [1]8.3  | 194 | —   | —   | —  |
|    | [2]22.2 | 250 | —   | 750 | K  |
|    | [F]30.5 | 444 | —   | 750 |    |
| 19 | [1]7.6  | 131 | 39  | —   | —  |
|    | [2]22.8 | 170 | 50  | 800 | R  |
|    | [F]30.4 | 301 | 89  | 800 |    |
| 20 | [1]8.2  | 156 | 47  | —   | —  |
|    | [2]21.8 | 200 | 60  | 800 | R  |
|    | [F]30.0 | 356 | 107 | 800 |    |
| 21 | [1]8.1  | —   | 77  | —   | —  |
|    | [2]23.0 | —   | 100 | 750 | K  |
|    | [F]31.1 | —   | 177 | 750 |    |
| 22 | [1]13.1 | 139 | 41  | —   | —  |
|    | [2]18.2 | 170 | 50  | 800 | Q  |
|    | [F]31.3 | 309 | 91  | 800 |    |
| 23 | [1]13.4 | 196 | 41  | —   | —  |
|    | [2]18.2 | 240 | 50  | 800 | Q  |
|    | [F]31.6 | 436 | 91  | 800 |    |

Explanation of Table V.

The notation [1] means the target amount of material to be deposited in the first impregnation (based on the final weight of the catalyst) and [2] means the target amount of material to be deposited in the second impregnation. The notation [F] means the target amount of material in the final catalyst. It is likely with the double impregnation process that some material is redissolved and hence the promoter concentration may be overstated. The amount of each of the anion components is with reference to the amount of cation (cesium) present.

TABLE VI

| | Calculated Catalyst Performance at Eighth Day at ΔEO of 2.0%[c] | | Calculated Aging Rate | |
|---|---|---|---|---|
| Example | Temp. °C. | Eff., % | % EO/day[d] | % Eff./day[e] |
| 6   | 258 | 78.4 | −0.046 | 0.0 |
| 7   | 245 | 79.3 | −0.011 | −0.04 |
| 8   | 241 | 79.3 | −0.021 | +0.04 |
| 9   | 251 | 78.3 | −0.027 | −0.30 |
| 10  | 253 | 77.1 | −0.033 | −0.05 |
| 11  | 245 | 79.3 | 0.0 | −0.01 |
| 12  | 257 | 77.7 | −0.011 | +0.20 |
| 13[a] | 261 | 73.5 | −0.1 | — |
| 14  | 241 | 80.3 | −0.02 | −0.07 |
| 15  | 255 | 76.8 | −0.1 | −0.28 |
| 16  | 239 | 80.0 | −0.016 | −0.067 |
| 17  | 247 | 79.0 | −0.017 | −0.035 |
| 18  | 250 | 76.3 | −0.011 | −0.087 |
| 19  | 247 | 77.3 | −0.026 | +0.035 |
| 20  | 251 | 76.0 | −0.023 | [b] |
| 21  | 253 | 78.4 | −0.01 | −0.52 |
| 22  | 240 | 78.8 | −0.025 | +0.029 |
| 23  | 246 | 76.7 | −0.019 | 0.0 |

[a]6 percent carbon dioxide, ΔEO is 1.43
[b]reactor system difficulties
[c]temperature and efficiency calculated by interpolation or extrapolation from generated data to provide consistent basis for comparison at 2.0 percent delta ethylene oxide
[d]calculated activity aging rates at constant temperatures
[e]calculated efficiency aging rates based on adjusted efficiencies at 2 mole % ethylene oxide EXAMPLES 24 to 26

Two stock solutions are prepared as follows:

Stock Solution 88:

11.47 parts by weight ethylene diamine 20.00 parts by weight water 11.60 parts by weight oxalic acid 19.82 parts by weight silver oxide 4.01 parts by weight monoethanol amine Stock Solution 115:

11.43 parts by weight ethylene diamine 24.00 parts by weight water 11.60 parts by weight oxalic acid 19.82 parts by weight silver oxide 4.00 parts by weight monoethanol amine In the preparation of the stock solutions, the feed rate of the oxalic acid and silver oxide are such that the temperature of the solution does not exotherm to greater than about 42° C.

From a portion of the stock solutions are prepared three impregnating solutions of the compositions set forth in Table VII.

TABLE VII

| Component | Example 24 (comparative) | Example 25 | Example 26 |
|---|---|---|---|
| Stock Solution 88 | 190.25 | 178.88 | — |
| Stock Solution 115 | — | — | 181.57 |
| $KNO_3$ | 1.1254 | 1.0452 | 1.0175 |
| $KMnO_4$ | — | 0.1174 | — |
| $Mn(NO_3)_2$ | — | — | 0.3674 |

The catalyst is prepared using a double impregnation technique in which a weighed amount of Carrier S is added to an impregnation vessel. The vessel containing the carrier is evacuated as in Example 1 and the designated stock solution is added. Then the vacuum is released to atmospheric pressure. The support is then drained and calcined as in Example 1 on a belt roaster. The catalyst is returned to the impregnation vessel for the second impregnation. The designated impregnation solution is added to the impregnation vessel while the vessel is maintained under vacuum as in Example 1. In the preparation of the impregnating solutions, the potassium nitrate is added first under vigorous stirring. The manganese-containing compound is then added under stirring and the impregnating solution is promptly used. The pressure in impregnation vessel is released to atmospheric pressure. The catalyst is drained and calcined as described above. The details of the catalyst preparation procedures and the resulting catalyst are summarized below:

|  | Example 24 | Example 25 | Example 26 |
|---|---|---|---|
| First Impregnation: | | | |
| Carrier (weight parts) | 61.10 | 61.07 | 61.24 |
| Stock Solution 88 (weight parts) | 192.5 | 193.2 | — |
| Stock Solution 115 (weight parts) | — | — | 188.3 |
| Vacuum (mm Hg) | 30 | 30 | 30 |
| Impregnation Time (min) | 30 | 30 | 30 |
| Drain Time (min) | 15 | 15 | 15 |
| Second Impregnation: | | | |
| Impregnating Solution (weight parts) | 191.38 | 180.04 | 182.95 |
| Vacuum (mm Hg) | 30 | 30 | 30 |
| Impregnation Time (min) | 30 | 30 | 30 |
| Drain Time (min) | 15 | 15 | 15 |
| Analysis: | | | |
| Silver (wt %) | 35.3 | 33.5 | 33.5 |
| Potassium (ppm based on K) | 1405 | 1314 | 1350 |
| Manganese (ppm based on Mn) | — | 136 | 334 |
| Sodium (ppm based on $N_2$) | 25 | 35 | 20 |

Each of the prepared catalysts are evaluated in autoclaves as described above using approximately 80 cubic centimeters of catalyst. The gas feed composition to the autoclave is 8 volume percent oxygen, 30 volume percent ethylene, about 5 ppmv ethylchloride, about 5 ppmv NO and the balance nitrogen. When the catalysts are started, the temperature is increased over a four day period (220°, 230°, 240° and 255° C.) to the final temperature of 255° C. The concentrations of ethylene chloride and nitrogen oxide are optimized for the combination of activity and efficiency. After 25 days of operation, the activity in producing ethylene oxide of the catalyst of Example 24 had dropped to about 70 percent of its value at day five, whereas the activities of the catalysts of Examples 25 and 26 remained approximately the same as those at day five, i.e., within about 5 percent of the day five activities.

EXAMPLES 27 to 43

The catalyst preparation and evaluation procedures of Examples 6 to 23 are essentially repeated except that all cesium salts are added in the second impregnation, and the catalysts are calcined at 300° C. for five minutes after each impregnation. Carrier U is used for the catalysts. The catalyst compositions and performances are summarized in Table VIII.

TABLE VIII

| Example | Total Cs (ppm) | ppm Cs as $Cs_2MoO_4$ | ppm Cs as $Cs_2SO_4$ | ppm Cs as $CsMnO_4$ | 1.5% EO* Temp, °C. | Eff, % | Decline Δ%EO† |
|---|---|---|---|---|---|---|---|
| 27 | 600 | 400 | 200 | — | 248 | 83.3 | 0.64 |
| 28 | 600 | 400 | 200 | — | 244 | 81.9 | 0.47 |
| 29 | 700 | 500 | 200 | — | 259 | 83.8 | 0.78 |
| 30 | 800 | 400 | 400 | — | 246 | 82.1 | 0.61 |
| 31 | 800 | 500 | 300 | — | 256 | 83.3 | 0.82 |
| 32 | 800 | 600 | 200 | — | 276 | 82.2 | 0.96 |
| 33 | 700 | 400 | 200 | 100 | 250 | 80.2 | 0.64 |
| 34 | 700 | 500 | 100 | 100 | 255 | 80.9 | 0.56 |
| 35 | 700 | 500 | 150 | 50 | 252 | 81.6 | 0.57 |
| 36 | 700 | 300 | 300 | 100 | 246 | 81.5 | 0.35 |
| 37 | 800 | 500 | 200 | 100 | 268 | 79.2 | 0.58 |
| 38 | 800 | 400 | 200 | 200 | 262 | 75.7 | 0.71 |
| 39 | 800 | 400 | 300 | 100 | 259 | 81.8 | 0.42 |
| 40 | 900 | 300 | 200 | 400 | 276 | <72.9 | (0.75**) |

TABLE VIII-continued

| | | | | 1.5% EO* | | |
| Example | Total Cs (ppm) | ppm Cs as Cs$_2$MoO$_4$ | ppm Cs as Cs$_2$SO$_4$ | ppm Cs as CsMnO$_4$ | Temp, °C. | Eff, % | Decline Δ%EO† |
|---|---|---|---|---|---|---|---|
| 41 | 900 | 400 | 200 | 300 | 266 | 75.5 | 0.48 |
| 42 | 900 | 400 | 400 | 100 | 249 | 81.8 | 0.58 |
| 43 | 1300 | 400 | 800 | 100 | 262 | 80.5 | 0.59 |

*Performance on day 7
8% O$_2$, 30% C$_2$H$_4$, 6.5% CO$_2$, 2 ppm ECl, 0.5% C$_2$H$_6$, 8000 GHSV, 275 psig.
†Change of % EO in 5 days at day 8.
**Estimated from 4-day test data.

EXAMPLES 44 to 50

Table IX below summarizes the details about the catalyst and the efficiencies at CONDITIONS. It should be appreciated that the catalyst performance characterized in these examples were not reflective of optimization of catalyst formulation.

The catalysts are prepared using the general procedures set forth below.

Impregnation Solution Preparation

1. Ethylenediamine (high purity grade) is mixed with distilled water.

2. Oxalic acid (oxalic acid dihydrate, reagent grade) is slowly added to the aqueous ethylenediamine solution at ambient conditions. An exothermic reaction occurs and the solution temperature rises to about 40° C.

3. Silver oxide is then added slowly to the solution of step 2.

4. To the solution in 3 above is added the monoethanolamine (Fe and Cl free). Steps 1 to 4 were performed in a large batch in a commercial catalyst manufacturing facility. Small portions of the impregnating solution are then used in the laboratory to prepare the catalysts. The weight ratios of ethylenediamine, oxalic acid (dihydrate), silver oxide and monethanolamine are 0.6:0.6: 1:0.2. Enough water is added to bring the silver concentration to 25.60% by weight. Small portions of this solution are used in the laboratory to prepare the catalysts.

5. The alkali metal salts are then added.

Impregnation of Carrier

1. The carrier is evacuated at room temperature and the impregnation solution above is added to the carrier under vacuum. Carrier T is used.

2. The excess solution is drained off.

Catalyst Roasting

1. The impregnation carrier is roasted in hot air using a belt roaster at about 500° C. for 2.5 minutes. Air flow is 66 SCFH/in$^2$.

The catalysts are tested at STANDARD ETHYLENE OXIDE PROCESS CONDITIONS under air conditions.

A summary of Examples 44 to 50 is provided in Table IX. As can be seen, if too much or too little manganese component is added, the performance of the catalyst can suffer.

TABLE IX

| | | wt ppm Cs | | | | | Air Conditions * | | | |
|---|---|---|---|---|---|---|---|---|---|---|
| Example | Ag wt % | total | as MoO4 | as MnO4 | as SO4 | day | T °C. | Effic. % | aging °C./d | % Eff/d |
| 44 | 21.4 | 517 | 206 | 154 | 157 | 2 | 264 | 73.7 | 2 | −0.5 |
| 45 | 21.4 | 520 | 310 | 159 | 51 | 2 | 276 | 71.6 | 2 | −0.3 |
| 46 | 20.4 | 492 | 246 | 99 | 147 | 2 | 257 | 74.9 | 1.35 | −0.18 |
| 47 | 20.6 | 496 | 199 | 48 | 249 | 2 | 256 | 74.8 | 0.76 | −0.05 |
| 48 | 20.6 | 499 | 296 | 54 | 149 | 2 | 266 | 73.2 | 3.2 | −0.7 |
| 49 | 21.2 | 518 | 256 | 30 | 232 | 2 | 267 | 74.4 | 2.82 | −0.75 |
| 50 (comparative) | 21.6 | 521 | 260 | 0 | 261 | 2 | 269 | 72 | 2.9 | −0.7 |

* inlet ethylene chloride, 2 ppmv; 1.4% EO outlet

EXAMPLES 51 and 52

The following general procedure is used to prepare the catalysts of Examples 51 and 52 (comparative).

To a 150 milliliter beaker with constant stirring are added:

36.72 grams ethylenediamine 25.00 ml water 36.83 grams oxalic acid 63.94 grams silver oxide 13.57 grams monoethanolamine The beaker is covered with a watch glass. The temperature of the solution after each ranges from 25° C. to 60° C. as the mixture is prepared. This mixture is then diluted with distilled water to 125 milliliters.

Ten grams of Carrier O are added to an impregnating chamber. The pressure of the chamber is reduced to a pressure of about 2.0–5.0 mm Hg absolute. About 31.25 milliliters of the impregnating solution are slowly added to the chamber. The pressure of the chamber is allowed to rise back to atmospheric. The impregnating solution is drained after 30 minutes. The impregnated support is calcined in a belt roaster as described above at 500° C. for 2.5 minutes.

The impregnating and roasting steps are repeated using a 31.25 milliliter aliquot of fresh impregnating solution which also contains rubidium salts. The catalyst of Example 51 is prepared from a solution containing 0.8217 gram of rubidium nitrate and 0.0854 gram of rubidium permanganate and the catalyst of Example 52 is prepared from a solution containing 0.8217 gram of rubidium nitrate. The final catalyst of Example 51 contains about 40 weight percent silver and 9273 ppmw rubidium nitrate, calculated as rubidium. The final catalyst of Example 52 contains about 40 weight percent silver and 8340 ppmw rubidium nitrate, calculated as rubidium.

The catalysts are used in a microreactor to evaluate performance. For the microreactor test, catalyst pills are crushed with a mortar and pestle and screened to the desired size (14–28 mesh). About 0.9 gram of crushed catalyst is loaded into a ¼ inch diameter by 5½ inch long stainless steel tube. The tube is placed inside a test oven and connected to a gas feed system. The temperature of the oven is controlled by a temperature controller and the reactor outlet pressure is controlled by a Groves back pressure regulator. The gas flow rate is adjusted to the desired gas hourly space velocity (6 liters per hour at standard temperature and pressure). The reaction temperature is measured with two thermocouples inside the reactor. One measures the inlet gas temperature, the other the outlet gas temperature. The reaction is controlled by the inlet gas temperature.

The feed composition contains 30 volume percent ethylene, 8 volume percent oxygen, about 5 to 6 ppmv ethyl chloride and about 6 ppmv NO. At 220° C. reactor temperature, at day 12 of operation, the catalyst of Example 52 has an activity of about ⅓ the activity provided by the catalyst of Example 51.

EXAMPLE 53

A catalyst similar to that prepared in Example 24 is operated under the conditions set forth in Example 24 for about 11 days with a reaction temperature of about 255° C. The catalyst has deactivated in activity during the period of operation. The catalyst is removed from the reaction equipment and treated with $KMnO_4$ dissolved in ethylenediamine by the incipient wetness technique such that the catalyst contained about 200 ppmw manganese based on the total catalyst weight. The catalyst is again subjected to the ethylene oxide producing conditions set forth in Example 24. The activity and efficiency exhibited by the catalyst are less than those when the catalyst was removed from reaction equipment; however, the activity appears to stabilize and after an additional 15 days of operation has an activity comparable to that expected for the catalyst had the catalyst not been treated with the potassium permanganate.

The manganate component may be added during the catalyst preparation or to a previously prepared, and even used, catalyst.

It is claimed:

1. A catalyst for the manufacture of alkylene oxide by the epoxidation of alkene containing an impregnated silver metal on an inert, refractory solid support; at least one promoter to enhance the efficiency of the catalyst, said efficiency promoter being a compound comprising at least one alkali metal, alkaline earth metal or oxyanion of an element other than manganese or oxygen selected from groups 3b through 7b and 3a through 7a of the Periodic Table and wherein the efficiency promoter comprises sulfate or molybdate or sulfate and molybdate; and a sufficient amount of manganese component to enhance at least one of catalyst activity, efficiency and stability as compared to a similar catalyst but which does not contain the manganese component, said comparison being under STANDARD ETHYLENE OXIDE PROCESS CONDITIONS.

2. A catalyst for the manufacture of alkylene oxide by the epoxidation of alkene containing an impregnated silver metal on an inert, refractory solid support; at least one promoter to enhance the efficiency of the catalyst, wherein the efficiency promoter comprises oxyanions of elements other than oxygen having an atomic number of 5 to 83 and being from the groups 3b through 7b, inclusive, and 3a through 7a, inclusive of the Periodic Table of the Elements; and a sufficient amount of manganese component to enhance at least one of catalyst activity, efficiency and stability as compared to a similar catalyst but which does not contain the manganese component, said comparison being under STANDARD ETHYLENE OXIDE PROCESS CONDITIONS, and in which at least about 60 ppmw of manganese component calculated on the weight of manganese are present based on the weight of the catalyst.

3. A catalyst for the manufacture of alkylene oxide by the epoxidation of alkene containing an impregnated silver metal on an inert, refractory solid support; one or more promoters to enhance the efficiency of the catalyst, said efficiency-enhancing promoters being compounds comprising at least one alkali metal, alkaline earth metal, or oxyanion of an element other than manganese and oxygen selected from groups 3b through 7b, inclusive, and 3a through 7a, inclusive of the Periodic Table; and a sufficient amount of manganese component to enhance at least one of catalyst activity, efficiency and stability as compared to a similar catalyst but which does not contain the manganese component, said comparison being under STANDARD ETHYLENE OXIDE PROCESS CONDITIONS, wherein said catalyst has a leachable potassium content of less than 25 ppmw based on the total weight of the catalyst, and in which the efficiency-enhancing promoters comprise sulfate or a molybdenum-containing oxyanion or sulfate and a molybdenum-containing oxyanion.

4. The catalyst of claim 3 in which the efficiency-enhancing promoters further comprise cesium.

5. A catalyst for the manufacture of alkylene oxide by the epoxidation of alkene containing an impregnated silver metal on an inert, refractory solid support; one or more promoters to enhance the efficiency of the catalyst, said efficiency-enhancing promoters being compounds comprising at least one alkali metal, alkaline earth metal, or oxyanion of an element other than manganese and oxygen selected from groups 3b through 7b, inclusive, and 3a through 7a, inclusive of the Periodic Table; and a sufficient amount of manganese component to enhance at least one of catalyst activity, efficiency and stability as compared to a similar catalyst but which does not contain the manganese component, said comparison being under STANDARD ETHYLENE OXIDE PROCESS CONDITIONS, wherein said catalyst has a leachable potassium content of less than 25 ppmw based on the total weight of the catalyst, and in which at least about 60 ppmw of manganese component calculated on the weight of manganese are present based on the weight of the catalyst.

6. The catalyst of claim 1 which further comprises sulfate in an amount sufficient to enhance the efficiency of the catalyst.

7. The catalyst of claim 6 in which the sulfate comprises fluorosulfate.

8. A catalyst for the manufacture of alkylene oxide by the epoxidation of alkene containing an impregnated silver metal on an inert, refractory solid support; at least one promoter to enhance the efficiency of the catalyst, and a sufficient amount of activity-enhancing manganese component to increase the activity of the catalyst, said efficiency-enhancing promoter being a compound comprising at least one alkali metal, alkaline earth metal or oxyanion of an element other than manganese and oxygen as determined under STANDARD ETHYLENE OXIDE PROCESS CONDITIONS, by at least about 5° C., as compared to a similar catalyst but which does not contain the manganese component, in which the manganese component comprises oxyanion of manganese, wherein the efficiency-enhancing promoter comprises oxyanions of elements other than oxygen having an atomic number of 5 to 83 and being from the groups 3b through 7b, inclusive, and 3a through 7a, inclusive, of the Periodic Table of the Elements, and in which the oxyanions comprise sulfate or molybdate or sulfate and molybdate.

9. The catalyst of claim 8 wherein the efficiency-enhancing promoter comprises alkali or alkaline earth metal cation.

10. The catalyst of claim 8 in which the efficiency-enhancing promoter enhances efficiency but decreases activity of the catalyst as determined under STANDARD ETHYLENE OXIDE PROCESS CONDITIONS.

11. A catalyst for the manufacture of alkylene oxide by the epoxidation of alkene containing an impregnated silver metal on an inert, refractory solid support, a sufficient amount of rhenium component to enhance at least one of efficiency and activity of the catalyst as compared to similar catalyst which does not contain the rhenium component and a sufficient amount of manganese component to enhance at least one of catalyst activity and stability as compared to a similar catalyst which does not contain the manganese component, said comparisons being under STANDARD ETHYLENE OXIDE PROCESS CONDITIONS.

12. The catalyst of claim 11 wherein the manganese component comprises oxyanion of manganese.

13. The catalyst of claim 11 wherein the rhenium component comprises rhenate.

14. The catalyst of claim 11 which further contains at least one other promoter to enhance the efficiency of the catalyst.

15. The catalyst of claim 14 in which the other promoter comprises alkali or alkaline earth metal cation.

16. The catalyst of claim 14 in which the other promoter enhances efficiency but decreases activity of the catalyst as determined under STANDARD ETHYLENE OXIDE PROCESS CONDITIONS.

17. The catalyst of claim 16 in which the other promoter comprises oxyanions of elements other than oxygen having an atomic number of 5 to 83 and being from the groups 3b through 7b, inclusive, and 3a through 7a, inclusive, of the Periodic Table of the Elements.

18. The catalyst of claim 17 in which the oxyanions comprise sulfate.

19. The catalyst of claim 16 in which at least about 60 ppmw of manganese component calculated on the weight of manganese are present based on the weight of the catalyst.

20. The catalyst of claim 11 which has a leachable potassium content of less than about 50 ppmw based on the total weight of the catalyst.

21. The catalyst of claim 12 which has a leachable potassium content of less than about 50 ppmw based on the total weight of the catalyst.

22. The catalyst of claim 14 which has a leachable potassium content of less than about 50 ppmw based on the total weight of the catalyst.

23. The catalyst of claim 18 which has a leachable potassium content of less than about 50 ppmw based on the total weight of the catalyst.

24. The catalyst of claim 13 in which the rhenium component is present in an amount between about 10 and 2000 ppmw calculated as the weight of rhenium based on the total weight of the catalyst.

25. The catalyst of claim 16 in which the rhenium component is present in an amount between about 10 and 2000 ppmw calculated as the weight of rhenium based on the total weight of the catalyst.

26. The catalyst of claim 18 in which the rhenium component is present in an amount between about 10 and 2000 ppmw calculated as the weight of rhenium based on the total weight of the catalyst.

27. The catalyst of claim 26 in which at least about 60 ppmw of manganese component calculated on the weight of manganese are present based on the weight of the catalyst.

28. The catalyst of claim 27 which has a leachable potassium content of less than about 25 ppmw based on the total weight of the catalyst.

29. The catalyst of claim 27 which further comprises cesium as a promoter.

30. The catalyst of claim 18 which further comprises cesium as a promoter.

31. The catalyst of claim 11 which further comprises sulfate in an amount sufficient to enhance efficiency.

32. The catalyst of claim 31 in which the sulfate comprises fluorosulfate.

33. A catalyst for the manufacture of alkylene oxide by the epoxidation of alkene containing an impregnated silver metal on an inert, refractory solid support; an efficiency-enhancing amount of at least one efficiency-enhancing salt of a member of a redox-half reaction pair; and a sufficient amount of manganese component to enhance at least one of catalyst activity and stability as compared to a similar catalyst but which does not contain the manganese component, said comparison being under STANDARD ETHYLENE OXIDE PROCESS CONDITIONS.

34. The catalyst of claim 33 in which the manganese component comprises oxyanion of manganese.

35. The catalyst of claim 33 in which the efficiency-enhancing salt of a member of a redox-half reaction pair comprises alkali metal nitrate.

36. The catalyst of claim 35 in which the alkali metal nitrate comprises at least one of potassium nitrate and rubidium nitrate.

37. The catalyst of claim 36 in which the alkali metal nitrate comprises potassium nitrate.

38. The catalyst of claim 37 in which the efficiency-enhancing salt, calculated as cation, is about 0.01 to about 5 percent by weight of the total weight of the catalyst.

39. The catalyst of claim 33 in which the efficiency-enhancing salt, calculated as cation, is about 0.01 to about 5 percent by weight of the total weight of the catalyst.

* * * * *